United States Patent [19]
Fukuda et al.

[11] Patent Number: 6,025,467
[45] Date of Patent: Feb. 15, 2000

[54] PARATHYROID HORMONE DERIVATIVES AND THEIR USE

[75] Inventors: Tsunehiko Fukuda, Kyoto; Shizue Nakagawa, Osaka; Junko Habashita, Nagaokakyo; Shigehisa Taketomi, Ikeda, all of Japan

[73] Assignee: Takeda Chemical Industries, Ltd., Osaka, Japan

[21] Appl. No.: 09/044,536

[22] Filed: Mar. 19, 1998

Related U.S. Application Data

[62] Division of application No. 08/662,871, Jun. 12, 1996, abandoned.

[30] Foreign Application Priority Data

Jun. 15, 1995 [JP] Japan .................................. 7-148652

[51] Int. Cl.⁷ .............................. C07K 7/06; A61K 38/16
[52] U.S. Cl. ............................................ 530/324; 514/12
[58] Field of Search ................................ 530/324; 514/12

[56] References Cited

FOREIGN PATENT DOCUMENTS

| | | |
|---|---|---|
| 0 477 885 A2 | 4/1992 | European Pat. Off. . |
| 0 528 271 A1 | 2/1993 | European Pat. Off. . |
| 0 561 412 A1 | 9/1993 | European Pat. Off. . |
| 2269176 | 2/1994 | United Kingdom . |
| WO 92/00753 | 1/1992 | WIPO . |
| WO 93/06845 | 4/1993 | WIPO . |
| WO 93/06846 | 4/1993 | WIPO . |

*Primary Examiner*—Cecilia J. Tsang
*Assistant Examiner*—Michael Borin
*Attorney, Agent, or Firm*—David G. Conlin; Christine C. O'Day

[57] ABSTRACT

Disclosed is a parathyroid hormone (PTH) (1–34) derivative in which at least the amino acid residue at the 10-position is substituted by an acidic amino acid residue. The derivatives of the present invention showing potent cAMP-producing activity and bone formation activity, and thus are useful as therapeutic agents for bone diseases, etc.

12 Claims, No Drawings

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 34 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: partial peptide
      (B) LOCATION: 1..34

(xi) SEQUENCE DESCRIPTION: SEQ ID NO:1:

-continued

```
Ser Val Ser Glu Ile Gln Leu Met His Asn Leu Gly Lys His Leu Asn
1               5                  10                  15

Ser Met Glu Arg Val Glu Trp Leu Arg Lys Lys Leu Gln Asp Val His
                20                  25                  30

Asn Phe
```

(2) INFORMATION FOR SEQ ID NO:2:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 10
        (D) OTHER INFORMATION: Xaa=acidic amino acid;

(ix) FEATURE:
        (A) NAME/KEY: Modified-site
        (B) LOCATION: 11
        (D) OTHER INFORMATION: Xaa=hydrophobic alpha amino acid,
            basic amino acid;

(ix) FEATURE:
        (A) NAME/KEY: Modified-site
        (B) LOCATION: 12
        (D) OTHER INFORMATION: Xaa=Gly, Ala, Ser, Lys, Orn;

(ix) FEATURE:
        (A) NAME/KEY: Modified-site
        (B) LOCATION: 13
        (D) OTHER INFORMATION: Xaa= basic amino acid;

(ix) FEATURE:
        (A) NAME/KEY: Modified-site
        (B) LOCATION: 14
        (D) OTHER INFORMATION: Xaa= basic amino acid;

(ix) FEATURE:
        (A) NAME/KEY: Modified-site
        (B) LOCATION: 15
        (D) OTHER INFORMATION: Xaa= aliphatic neutral amino acid,
            basic amino acid;

(ix) FEATURE:
        (A) NAME/KEY: Modified-site
        (B) LOCATION: 16,17
        (D) OTHER INFORMATION: Xaa= non-charged hydrophilic amino
            acid-basic amino acid;

(ix) FEATURE:
        (A) NAME/KEY: Modified-site
        (B) LOCATION: 19
        (D) OTHER INFORMATION: Xaa= acidic amino acid, basic amino
            acid;

(ix) FEATURE:
        (A) NAME/KEY: Modified-site
        (B) LOCATION: 21
        (D) OTHER INFORMATION: Xaa= aliphatic neutral amino acid,
            basic amino acid;
        (B) LOCATION: 26
        (D) OTHER INFORMATION: Xaa= basic amino acid;

(ix) FEATURE:
        (A) NAME/KEY: Modified-site
        (B) LOCATION: 27
        (D) OTHER INFORMATION: Xaa= non-charged hydrophilic amino
            acid, basic amino acid;

(ix) FEATURE:
        (A) NAME/KEY: Modified-site (B) LOCATION: 30
        (D) OTHER INFORMATION: Xaa= acidic amino acid, aliphatic
            neutral amino acid;

(ix) FEATURE:
        (A) NAME/KEY: Modified-site
        (B) LOCATION: 34
        (D) OTHER INFORMATION: Xaa= aromatic amino acid.

(xi) SEQUENCE DESCRIPTION: SEQ ID NO:2:

Ser Val Ser Glu Ile Gln Leu Met His Xaa Xaa Xaa Xaa Xaa Xaa
1               5                   10                  15

Xaa Met Xaa Arg Xaa Glu Trp Leu Arg Xaa Xaa Leu Gln Xaa Val His
            20                  25                  30

Asn Xaa (2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..4

(xi) SEQUENCE DESCRIPTION: SEQ ID NO:3:

Phe Val Ala Leu
1

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..5

(xi) SEQUENCE DESCRIPTION: SEQ ID NO:4:

Phe Val Ala Leu Gly
1               5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..6

(xi) SEQUENCE DESCRIPTION: SEQ ID NO:5:

Phe Val Ala Leu Gly Ala
1               5

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..7

(xi) SEQUENCE DESCRIPTION: SEQ ID NO:6:

Phe Val Ala Leu Gly Ala Pro
1               5

(2) INFORMATION FOR SEQ ID NO:7:

(i) SEQUENCE CHARACTERISTICS:
        (A) LENGTH: 51 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..51

(xi) SEQUENCE DESCRIPTION: SEQ ID NO:7:

Phe Val Ala Leu Gly Ala Pro Leu Ala Pro Arg Asp Ala Gly Ser Gln
1               5                   10                  15

Arg Pro Arg Lys Lys Glu Asp Asn Val Leu Val Glu Ser His Glu Lys
            20                  25                  30

Ser Leu Gly Glu Ala Asp Lys Ala Asp Val Asn Val Leu Thr Lys Ala
        35                  40                  45

Lys Ser Gln
    50

(2) INFORMATION FOR SEQ ID NO:8:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(xi) SEQUENCE DESCRIPTION: SEQ ID NO:8:

Ser Val Ser Glu Ile Gln Leu Met His Asp Lys Gly Lys His Leu Asn
1               5                   10                  15

Ser Met Glu Arg Val Glu Trp Leu Arg Lys Lys Leu Gln Asp Val His
            20                  25                  30

Asn Phe (2) INFORMATION FOR SEQ ID NO:9:

(i) SEQUENCE CHARACTERISTICS:
        (A) LENGTH: 34 amino acids

```
            (B) TYPE: amino acid
            (C) STRANDEDNESS:
            (D) TOPOLOGY: linear (ii) MOLECULE TYPE: peptide (ix) FEATURE:
           (A) NAME/KEY: partial peptide
           (B) LOCATION: 1..34

(xi) SEQUENCE DESCRIPTION: SEQ ID NO:9:

Ser Val Ser Glu Ile Gln Leu Met His Asp Leu Gly Lys His Leu Asn
1               5                  10                  15

Ser Met Glu Arg Val Glu Trp Leu Arg Lys Lys Leu Gln Asp Val His
            20                  25                  30

Asn Phe (2) INFORMATION FOR SEQ ID NO:10:

(i) SEQUENCE CHARACTERISTICS:
           (A) LENGTH: 34 amino acids
           (B) TYPE: amino acid
           (C) STRANDEDNESS:
           (D) TOPOLOGY: linear (ii) MOLECULE TYPE: peptide (ix) FEATURE:
           (A) NAME/KEY: partial peptide
           (B) LOCATION: 1..34

(xi) SEQUENCE DESCRIPTION: SEQ ID NO:10:

Ser Val Ser Glu Ile Gln Leu Met His Glu Leu Gly Lys His Leu Asn
1               5                  10                  15

Ser Met Glu Arg Val Glu Trp Leu Arg Lys Lys Leu Gln Asp Val His
            20                  25                  30

Asn Phe (2) INFORMATION FOR SEQ ID NO:11:

(i) SEQUENCE CHARACTERISTICS:
           (A) LENGTH: 34 amino acids
           (B) TYPE: amino acid
           (C) STRANDEDNESS:
           (D) TOPOLOGY: linear (ii) MOLECULE TYPE: peptide (ix) FEATURE:
           (A) NAME/KEY: partial peptide
           (B) LOCATION: 1..34

(xi) SEQUENCE DESCRIPTION: SEQ ID NO:11:

Ser Val Ser Glu Ile Gln Leu Met His Asp Phe Gly Lys His Leu Asn
1               5                  10                  15

Ser Met Glu Arg Val Glu Trp Leu Arg Lys Lys Leu Gln Asp Val His
            20                  25                  30

Asn Phe (2) INFORMATION FOR SEQ ID NO:12:

(i) SEQUENCE CHARACTERISTICS:
           (A) LENGTH: 34 amino acids
           (B) TYPE: amino acid
           (C) STRANDEDNESS:
           (D) TOPOLOGY: linear
```

```
        (ii) MOLECULE TYPE: peptide (ix) FEATURE:
             (A) NAME/KEY: partial peptide
             (B) LOCATION: 1..34

(ix) FEATURE:
             (A) NAME/KEY: Modified-site
             (B) LOCATION: 11
             (D) OTHER INFORMATION: /product= "Xaa=Ala(2-Naph)"

(xi) SEQUENCE DESCRIPTION: SEQ ID NO:12:

Ser Val Ser Glu Ile Gln Leu Met His Asp Xaa Gly Lys His Leu Asn
1               5                   10                  15

Ser Met Glu Arg Val Glu Trp Leu Arg Lys Lys Leu Gln Asp Val His
            20                  25                  30

Asn Phe (2) INFORMATION FOR SEQ ID NO:13:

(i) SEQUENCE CHARACTERISTICS:
            (A) LENGTH: 34 amino acids
            (B) TYPE: amino acid
            (C) STRANDEDNESS:
            (D) TOPOLOGY: linear (ii) MOLECULE TYPE: peptide (ix) FEATURE:
             (A) NAME/KEY: partial peptide
             (B) LOCATION: 1..34

(ix) FEATURE:
             (A) NAME/KEY: Modified-site
             (B) LOCATION: 10
             (D) OTHER INFORMATION: /product= "Xaa=4-carboxyglutamic
                 acid"

(xi) SEQUENCE DESCRIPTION: SEQ ID NO:13:

Ser Val Ser Glu Ile Gln Leu Met His Xaa Leu Gly Lys His Leu Asn
1               5                   10                  15

Ser Met Glu Arg Val Glu Trp Leu Arg Lys Lys Leu Gln Asp Val His
            20                  25                  30

Asn Phe (2) INFORMATION FOR SEQ ID NO:14:

(i) SEQUENCE CHARACTERISTICS:
            (A) LENGTH: 34 amino acids
            (B) TYPE: amino acid
            (C) STRANDEDNESS:
            (D) TOPOLOGY: linear (ii) MOLECULE TYPE: peptide (ix) FEATURE:
             (A) NAME/KEY: partial peptide
             (B) LOCATION: 1..34

(ix) FEATURE:
             (A) NAME/KEY: Modified-site
             (B) LOCATION: 10
             (D) OTHER INFORMATION: /product= "Xaa=2-aminosuberic acid"

(xi) SEQUENCE DESCRIPTION: SEQ ID NO:14:

Ser Val Ser Glu Ile Gln Leu Met His Xaa Leu Gly Lys His Leu Asn
1               5                   10                  15

Ser Met Glu Arg Val Glu Trp Leu Arg Lys Lys Leu Gln Asp Val His
            20                  25                  30
```

Asn Phe (2) INFORMATION FOR SEQ ID NO:15:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(ix) FEATURE:
        (A) NAME/KEY: Modified-site
        (B) LOCATION: 10
        (D) OTHER INFORMATION: /product= "2-aminoadipic acid"

(xi) SEQUENCE DESCRIPTION: SEQ ID NO:15:

Ser Val Ser Glu Ile Gln Leu Met His Xaa Leu Gly Lys His Leu Asn
1               5                   10                  15

Ser Met Glu Arg Val Glu Trp Leu Arg Lys Lys Leu Gln Asp Val His
                20                  25                  30

Asn Phe (2) INFORMATION FOR SEQ ID NO:16:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(xi) SEQUENCE DESCRIPTION: SEQ ID NO:16:

Ser Val Ser Glu Ile Gln Leu Met His Glu Leu Gly Lys His Leu Lys
1               5                   10                  15

Lys Met Glu Arg Val Glu Trp Leu Arg Lys Lys Leu Gln Asp Val His
                20                  25                  30

Asn Phe (2) INFORMATION FOR SEQ ID NO:17:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(xi) SEQUENCE DESCRIPTION: SEQ ID NO:17:

Ser Val Ser Glu Ile Gln Leu Met His Glu Leu Gly Lys His Leu Asn
1               5                   10                  15

Lys Met Glu Arg Val Glu Trp Leu Arg Lys Lys Leu Gln Asp Val His

```
            20                  25                  30

Asn Phe (2) INFORMATION FOR SEQ ID NO:18:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(xi) SEQUENCE DESCRIPTION: SEQ ID NO:18:

Ser Val Ser Glu Ile Gln Leu Met His Glu Leu Gly Lys His Leu Lys
1               5                  10                  15

Ser Met Glu Arg Val Glu Trp Leu Arg Lys Lys Leu Gln Asp Val His
            20                  25                  30

Asn Phe (2) INFORMATION FOR SEQ ID NO:19:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(xi) SEQUENCE DESCRIPTION: SEQ ID NO:19:

Ser Val Ser Glu Ile Gln Leu Met His Glu Leu Gly Lys His Leu Ser
1               5                  10                  15

Ser Met Glu Arg Val Glu Trp Leu Arg Lys Lys Leu Gln Asp Val His
            20                  25                  30

Asn Phe (2) INFORMATION FOR SEQ ID NO:20:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(xi) SEQUENCE DESCRIPTION: SEQ ID NO:20:

Ser Val Ser Glu Ile Gln Leu Met His Glu Leu Gly Lys His Leu Lys
1               5                  10                  15

Ser Met Glu Arg Val Glu Trp Leu Arg Lys Gln Leu Gln Asp Val His
            20                  25                  30

Asn Phe
```

(2) INFORMATION FOR SEQ ID NO:21:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(xi) SEQUENCE DESCRIPTION: SEQ ID NO:21:

```
Ser Val Ser Glu Ile Gln Leu Met His Glu Phe Gly Lys His Leu Lys
1               5                  10                  15

Ser Met Glu Arg Val Glu Trp Leu Arg Lys Gln Leu Gln Asp Val His
                20                  25                  30

Asn Phe
```

(2) INFORMATION FOR SEQ ID NO:22:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(ix) FEATURE:
        (A) NAME/KEY: Modified-site
        (B) LOCATION: 30
        (D) OTHER INFORMATION: /product= "Xaa=2-aminoisobutyric
            acid"

(xi) SEQUENCE DESCRIPTION: SEQ ID NO:22:

```
Ser Val Ser Glu Ile Gln Leu Met His Asp Phe Gly Lys His Leu Lys
1               5                  10                  15

Ser Met Glu Arg Val Glu Trp Leu Arg Lys Gln Leu Gln Xaa Val His
                20                  25                  30

Asn Phe
```

(2) INFORMATION FOR SEQ ID NO:23:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(ix) FEATURE:
        (A) NAME/KEY: Modified-site
        (B) LOCATION: 30
        (D) OTHER INFORMATION: /product= "Xaa=2-aminoisobutyric
            acid"

(xi) SEQUENCE DESCRIPTION: SEQ ID NO:23:

Ser Val Ser Glu Ile Gln Leu Met His Asp Phe Gly Lys His Leu Lys
1               5                   10                  15

Lys Met Glu Arg Val Glu Trp Leu Arg Lys Gln Leu Gln Xaa Val His
            20                  25                  30

Asn Phe (2) INFORMATION FOR SEQ ID NO:24:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(ix) FEATURE:
        (A) NAME/KEY: Modified-site
        (B) LOCATION: 30
        (D) OTHER INFORMATION: /product= "Xaa=2-aminoisobutyric
            acid"

(xi) SEQUENCE DESCRIPTION: SEQ ID NO:24:

Ser Val Ser Glu Ile Gln Leu Met His Asp Phe Gly Lys His Lys Lys
1               5                   10                  15

Ser Met Glu Arg Val Glu Trp Leu Arg Lys Gln Leu Gln Xaa Val His
            20                  25                  30

Asn Phe (2) INFORMATION FOR SEQ ID NO:25:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

(xi) SEQUENCE DESCRIPTION: SEQ ID NO:25:

Ser Val Ser Glu Ile Gln Leu Met His Glu Leu Gly Lys Lys Leu Asn
1               5                   10                  15

Ser Met Glu Arg Val Glu Trp Leu Arg Lys Lys Leu Gln Asp Val His
            20                  25                  30

Asn Phe (2) INFORMATION FOR SEQ ID NO:26:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: partial peptide
        (B) LOCATION: 1..34

```
    (ix) FEATURE:
         (A) NAME/KEY: Modified-site
         (B) LOCATION: 13
         (D) OTHER INFORMATION: /product= "Xaa=ornithine"

(xi) SEQUENCE DESCRIPTION: SEQ ID NO:26:

Ser Val Ser Glu Ile Gln Leu Met His Glu Leu Gly Xaa His Leu Asn
1               5                   10                  15

Ser Met Glu Arg Val Glu Trp Leu Arg Lys Lys Leu Gln Asp Val His
                20                  25                  30

Asn Phe (2) INFORMATION FOR SEQ ID NO:27:

(i) SEQUENCE CHARACTERISTICS:
         (A) LENGTH: 34 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: partial peptide
         (B) LOCATION: 1..34

(xi) SEQUENCE DESCRIPTION: SEQ ID NO:27:

Ser Val Ser Glu Ile Gln Leu Met His Asp Leu Gly Lys His Leu Asn
1               5                   10                  15

Ser Met Arg Arg Val Glu Trp Leu Arg Lys Lys Leu Gln Asp Val His
                20                  25                  30

Asn Phe (2) INFORMATION FOR SEQ ID NO:28:

(i) SEQUENCE CHARACTERISTICS:
         (A) LENGTH: 34 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: partial peptide
         (B) LOCATION: 1..34

(xi) SEQUENCE DESCRIPTION: SEQ ID NO:28:

Ser Val Ser Glu Ile Gln Leu Met His Asp Leu Gly Lys His Leu Asn
1               5                   10                  15

Ser Met Glu Arg Arg Glu Trp Leu Arg Lys Lys Leu Gln Asp Val His
                20                  25                  30

Asn Phe (2) INFORMATION FOR SEQ ID NO:29:

(i) SEQUENCE CHARACTERISTICS:
         (A) LENGTH: 34 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: partial peptide
         (B) LOCATION: 1..34
```

(xi) SEQUENCE DESCRIPTION: SEQ ID NO:29:

Ser Val Ser Glu Ile Gln Leu Met His Glu Leu Gly Lys His Leu Asn
1               5                   10                  15

Ser Met Glu Arg Val Glu Trp Leu Arg Arg Lys Leu Gln Asp Val His
                20                  25                  30

Asn Phe (2) INFORMATION FOR SEQ ID NO:30:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 10
        (D) OTHER INFORMATION: Xaa=acidic amino acid;

(ix) FEATURE:
        (A) NAME/KEY: Modified-site
        (B) LOCATION: 11
        (D) OTHER INFORMATION: Xaa=hydrophobic alpha amino acid, basic
           amino acid;

(ix) FEATURE:
        (A) NAME/KEY: Modified-site
        (B) LOCATION: 12
        (D) OTHER INFORMATION: Xaa=Gly, Ala, Ser, Lys, Orn;

(ix) FEATURE:
        (A) NAME/KEY: Modified-site
        (B) LOCATION: 13
        (D) OTHER INFORMATION: Xaa= basic amino acid;

(ix) FEATURE:
        (A) NAME/KEY: Modified-site
        (B) LOCATION: 14
        (D) OTHER INFORMATION: Xaa= basic amino acid;

(ix) FEATURE:
        (A) NAME/KEY: Modified-site
        (B) LOCATION: 15
        (D) OTHER INFORMATION: Xaa= aliphatic neutral amino acid,
           basic amino acid;

(ix) FEATURE:
        (A) NAME/KEY: Modified-site
        (B) LOCATION: 16,17
        (D) OTHER INFORMATION: Xaa= non-charged hydrophilic amino
           acid-basic amino acid;

(ix) FEATURE:
        (A) NAME/KEY: Modified-site
        (B) LOCATION: 19
        (D) OTHER INFORMATION: Xaa= acidic amino acid, basic amino
           acid;

(ix) FEATURE:
        (A) NAME/KEY: Modified-site
        (B) LOCATION: 21
        (D) OTHER INFORMATION: Xaa= aliphatic neutral amino acid,
           basic amino acid;

(ix) FEATURE:
        (A) NAME/KEY: Modified-site
        (B) LOCATION: 26
        (D) OTHER INFORMATION: Xaa= basic amino acid;

(ix) FEATURE:
        (A) NAME/KEY: Modified-site (B) LOCATION: 27
            (D) OTHER INFORMATION: Xaa= non-charged hydrophilic amino
                acid, basic amino acid;

(ix) FEATURE:
            (A) NAME/KEY: Modified-site
            (B) LOCATION: 30
            (D) OTHER INFORMATION: Xaa= acidic amino acid, aliphatic
                neutral amino acid;

(xi) SEQUENCE DESCRIPTION: SEQ ID NO:30:

Ser Val Ser Glu Ile Gln Leu Met His Xaa Xaa Xaa Xaa Xaa Xaa Xaa
1               5                   10                  15

Xaa Met Xaa Arg Xaa Glu Trp Leu Arg Xaa Xaa Leu Gln Xaa Val His
            20                  25                  30

Asn Phe Val
        35

(2) INFORMATION FOR SEQ ID NO:31:

(i) SEQUENCE CHARACTERISTICS:
            (A) LENGTH: 36 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 10
            (D) OTHER INFORMATION: Xaa=acidic amino acid;

(ix) FEATURE:
            (A) NAME/KEY: Modified-site
            (B) LOCATION: 11
            (D) OTHER INFORMATION: Xaa=hydrophobic alpha amino acid,
                basic amino acid;

(ix) FEATURE:
            (A) NAME/KEY: Modified-site
            (B) LOCATION: 12
            (D) OTHER INFORMATION: Xaa=Gly, Ala, Ser, Lys, Orn;

(ix) FEATURE:
            (A) NAME/KEY: Modified-site
            (B) LOCATION: 13
            (D) OTHER INFORMATION: Xaa= basic amino acid;

(ix) FEATURE:
            (A) NAME/KEY: Modified-site
            (B) LOCATION: 14
            (D) OTHER INFORMATION: Xaa= basic amino acid;

(ix) FEATURE:
            (A) NAME/KEY: Modified-site
            (B) LOCATION: 15
            (D) OTHER INFORMATION: Xaa= aliphatic neutral amino acid,
                basic amino acid;

(ix) FEATURE:
            (A) NAME/KEY: Modified-site
            (B) LOCATION: 16,17
            (D) OTHER INFORMATION: Xaa= non-charged hydrophilic amino
                acid-basic amino acid;

(ix) FEATURE:
            (A) NAME/KEY: Modified-site
            (B) LOCATION: 19
            (D) OTHER INFORMATION: Xaa= acidic amino acid, basic amino
                acid;

(ix) FEATURE:
            (A) NAME/KEY: Modified-site
            (B) LOCATION: 21

(D) OTHER INFORMATION: Xaa= aliphatic neutral amino acid,
                        basic amino acid;

(ix) FEATURE:
                    (A) NAME/KEY: Modified-site
                    (B) LOCATION: 26
                    (D) OTHER INFORMATION: Xaa= basic amino acid;

(ix) FEATURE:
                    (A) NAME/KEY: Modified-site
                    (B) LOCATION: 27
                    (D) OTHER INFORMATION: Xaa= non-charged hydrophilic amino
                        acid, basic amino acid;

(ix) FEATURE:
                    (A) NAME/KEY: Modified-site
                    (B) LOCATION: 30
                    (D) OTHER INFORMATION: Xaa= acidic amino acid, aliphatic
                        neutral amino acid;

(xi) SEQUENCE DESCRIPTION: SEQ ID NO:31:

Ser Val Ser Glu Ile Gln Leu Met His Xaa Xaa Xaa Xaa Xaa Xaa Xaa
1               5                   10                  15

Xaa Met Xaa Arg Xaa Glu Trp Leu Arg Xaa Xaa Leu Gln Xaa Val His
            20                  25                  30

Asn Phe Val Ala
        35

(2) INFORMATION FOR SEQ ID NO:32:

(i) SEQUENCE CHARACTERISTICS:
                    (A) LENGTH: 37 amino acids
                    (B) TYPE: amino acid
                    (C) STRANDEDNESS:
                    (D) TOPOLOGY: linear (ii) MOLECULE TYPE: peptide (ix) FEATURE:
                    (A) NAME/KEY: Modified-site
                    (B) LOCATION: 10
                    (D) OTHER INFORMATION: Xaa=acidic amino acid;

(ix) FEATURE:
                    (A) NAME/KEY: Modified-site
                    (B) LOCATION: 11
                    (D) OTHER INFORMATION: Xaa=hydrophobic alpha amino acid, basic
                        amino acid;

(ix) FEATURE:
                    (A) NAME/KEY: Modified-site
                    (B) LOCATION: 12
                    (D) OTHER INFORMATION: Xaa=Gly, Ala, Ser, Lys, Orn;

(ix) FEATURE:
                    (A) NAME/KEY: Modified-site
                    (B) LOCATION: 13
                    (D) OTHER INFORMATION: Xaa= basic amino acid;

(ix) FEATURE:
                    (A) NAME/KEY: Modified-site
                    (B) LOCATION: 14
                    (D) OTHER INFORMATION: Xaa= basic amino acid;

(ix) FEATURE:
                    (A) NAME/KEY: Modified-site
                    (B) LOCATION: 15
                    (D) OTHER INFORMATION: Xaa= aliphatic neutral amino acid,
                        basic amino acid;

(ix) FEATURE:
                    (A) NAME/KEY: Modified-site
                    (B) LOCATION: 16,17
                    (D) OTHER INFORMATION: Xaa= non-charged hydrophilic amino
                        acid-basic amino acid;

```
    (ix) FEATURE:
         (A) NAME/KEY: Modified-site
         (B) LOCATION: 19
         (D) OTHER INFORMATION: Xaa= acidic amino acid, basic amino
             acid;

(ix) FEATURE:
         (A) NAME/KEY: Modified-site
         (B) LOCATION: 21
         (D) OTHER INFORMATION: Xaa= aliphatic neutral amino acid,
             basic amino acid;

(ix) FEATURE:
         (A) NAME/KEY: Modified-site
         (B) LOCATION: 26
         (D) OTHER INFORMATION: Xaa= basic amino acid;

(ix) FEATURE:
         (A) NAME/KEY: Modified-site
         (B) LOCATION: 27
         (D) OTHER INFORMATION: Xaa= non-charged hydrophilic amino
             acid, basic amino acid;

(ix) FEATURE:
         (A) NAME/KEY: Modified-site
         (B) LOCATION: 30
         (D) OTHER INFORMATION: Xaa= acidic amino acid, aliphatic
             neutral amino acid;

(xi) SEQUENCE DESCRIPTION: SEQ ID NO:32:

Ser Val Ser Glu Ile Gln Leu Met His Xaa Xaa Xaa Xaa Xaa Xaa Xaa
1               5                   10                  15

Xaa Met Xaa Arg Xaa Glu Trp Leu Arg Xaa Xaa Leu Gln Xaa Val His
            20                  25                  30

Asn Phe Val Ala Leu
        35

(2) INFORMATION FOR SEQ ID NO:33:

(i) SEQUENCE CHARACTERISTICS:
        (A) LENGTH: 38 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 10
         (D) OTHER INFORMATION: Xaa=acidic amino acid;

(ix) FEATURE:
         (A) NAME/KEY: Modified-site
         (B) LOCATION: 11
         (D) OTHER INFORMATION: Xaa=hydrophobic alpha amino acid,
             basic amino acid;

(ix) FEATURE:
         (A) NAME/KEY: Modified-site
         (B) LOCATION: 12
         (D) OTHER INFORMATION: Xaa=Gly, Ala, Ser, Lys, Orn;

(ix) FEATURE:
         (A) NAME/KEY: Modified-site
         (B) LOCATION: 13
         (D) OTHER INFORMATION: Xaa= basic amino acid;

(ix) FEATURE:
         (A) NAME/KEY: Modified-site
         (B) LOCATION: 14
         (D) OTHER INFORMATION: Xaa= basic amino acid;

(ix) FEATURE:
```

(A) NAME/KEY: Modified-site
            (B) LOCATION: 15
            (D) OTHER INFORMATION: Xaa= aliphatic neutral amino acid,
                basic amino acid;

(ix) FEATURE:
            (A) NAME/KEY: Modified-site
            (B) LOCATION: 16,17
            (D) OTHER INFORMATION: Xaa= non-charged hydrophilic amino
                acid-basic amino acid;

(ix) FEATURE:
            (A) NAME/KEY: Modified-site
            (B) LOCATION: 19
            (D) OTHER INFORMATION: Xaa= acidic amino acid, basic amino
                acid;

(ix) FEATURE:
            (A) NAME/KEY: Modified-site
            (B) LOCATION: 21
            (D) OTHER INFORMATION: Xaa= aliphatic neutral amino acid,
                basic amino acid;

(ix) FEATURE:
            (A) NAME/KEY: Modified-site
            (B) LOCATION: 26
            (D) OTHER INFORMATION: Xaa= basic amino acid;

(ix) FEATURE:
            (A) NAME/KEY: Modified-site
            (B) LOCATION: 27
            (D) OTHER INFORMATION: Xaa= non-charged hydrophilic amino
                acid, basic amino acid;

(ix) FEATURE:
            (A) NAME/KEY: Modified-site
            (B) LOCATION: 30
            (D) OTHER INFORMATION: Xaa= acidic amino acid, aliphatic
                neutral amino acid;

(xi) SEQUENCE DESCRIPTION: SEQ ID NO:33:

Ser Val Ser Glu Ile Gln Leu Met His Xaa Xaa Xaa Xaa Xaa Xaa Xaa
1               5                   10                  15

Xaa Met Xaa Arg Xaa Glu Trp Leu Arg Xaa Xaa Leu Gln Xaa Val His
            20                  25                  30

Asn Phe Val Ala Leu Gly
            35

(2) INFORMATION FOR SEQ ID NO:34:

(i) SEQUENCE CHARACTERISTICS:
            (A) LENGTH: 39 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 10
            (D) OTHER INFORMATION: Xaa=acidic amino acid;

(ix) FEATURE:
            (A) NAME/KEY: Modified-site
            (B) LOCATION: 11
            (D) OTHER INFORMATION: Xaa=hydrophobic alpha amino acid,
                basic amino acid;

(ix) FEATURE:
            (A) NAME/KEY: Modified-site
            (B) LOCATION: 12
            (D) OTHER INFORMATION: Xaa=Gly, Ala, Ser, Lys, Orn;

(ix) FEATURE:

```
                (A) NAME/KEY: Modified-site
                (B) LOCATION: 13
                (D) OTHER INFORMATION: Xaa= basic amino acid;

(ix) FEATURE:
                (A) NAME/KEY: Modified-site
                (B) LOCATION: 14
                (D) OTHER INFORMATION: Xaa= basic amino acid;

(ix) FEATURE:
                (A) NAME/KEY: Modified-site
                (B) LOCATION: 15
                (D) OTHER INFORMATION: Xaa= aliphatic neutral amino acid,
                    basic amino acid;

(ix) FEATURE:
                (A) NAME/KEY: Modified-site
                (B) LOCATION: 16,17
                (D) OTHER INFORMATION: Xaa= non-charged hydrophilic amino
                    acid-basic amino acid;

(ix) FEATURE:
                (A) NAME/KEY: Modified-site
                (B) LOCATION: 19
                (D) OTHER INFORMATION: Xaa= acidic amino acid, basic amino
                    acid;

(ix) FEATURE:
                (A) NAME/KEY: Modified-site
                (B) LOCATION: 21
                (D) OTHER INFORMATION: Xaa= aliphatic neutral amino acid,
                    basic amino acid;

(ix) FEATURE:
                (A) NAME/KEY: Modified-site
                (B) LOCATION: 26
                (D) OTHER INFORMATION: Xaa= basic amino acid;

(ix) FEATURE:
                (A) NAME/KEY: Modified-site
                (B) LOCATION: 27
                (D) OTHER INFORMATION: Xaa= non-charged hydrophilic amino
                    acid, basic amino acid;

(ix) FEATURE:
                (A) NAME/KEY: Modified-site
                (B) LOCATION: 30
                (D) OTHER INFORMATION: Xaa= acidic amino acid, aliphatic
                    neutral amino acid;

(xi) SEQUENCE DESCRIPTION: SEQ ID NO:34:

Ser Val Ser Glu Ile Gln Leu Met His Xaa Xaa Xaa Xaa Xaa Xaa Xaa
1               5                   10                  15

Xaa Met Xaa Arg Xaa Glu Trp Leu Arg Xaa Xaa Leu Gln Xaa Val His
            20                  25                  30

Asn Phe Val Ala Leu Gly Ala
            35

(2) INFORMATION FOR SEQ ID NO:35:

(i) SEQUENCE CHARACTERISTICS:
                (A) LENGTH: 40 amino acids
                (B) TYPE: amino acid
                (C) STRANDEDNESS:
                (D) TOPOLOGY: linear (ii) MOLECULE TYPE: peptide (ix) FEATURE:
                (A) NAME/KEY: Modified-site
                (B) LOCATION: 10
                (D) OTHER INFORMATION: Xaa=acidic amino acid;

(ix) FEATURE:
                (A) NAME/KEY: Modified-site
```

(B) LOCATION: 11
            (D) OTHER INFORMATION: Xaa=hydrophobic alpha amino acid,
                basic amino acid;

(ix) FEATURE:
            (A) NAME/KEY: Modified-site
            (B) LOCATION: 12
            (D) OTHER INFORMATION: Xaa=Gly, Ala, Ser, Lys, Orn;

(ix) FEATURE:
            (A) NAME/KEY: Modified-site
            (B) LOCATION: 13
            (D) OTHER INFORMATION: Xaa= basic amino acid;

(ix) FEATURE:
            (A) NAME/KEY: Modified-site
            (B) LOCATION: 14
            (D) OTHER INFORMATION: Xaa= basic amino acid;

(ix) FEATURE:
            (A) NAME/KEY: Modified-site
            (B) LOCATION: 15
            (D) OTHER INFORMATION: Xaa= aliphatic neutral amino acid,
                basic amino acid;

(ix) FEATURE:
            (A) NAME/KEY: Modified-site
            (B) LOCATION: 16,17
            (D) OTHER INFORMATION: Xaa= non-charged hydrophilic amino
                acid-basic amino acid;

(ix) FEATURE:
            (A) NAME/KEY: Modified-site
            (B) LOCATION: 19
            (D) OTHER INFORMATION: Xaa= acidic amino acid, basic amino
                acid;

(ix) FEATURE:
            (A) NAME/KEY: Modified-site
            (B) LOCATION: 21
            (D) OTHER INFORMATION: Xaa= aliphatic neutral amino acid,
                basic amino acid;

(ix) FEATURE:
            (A) NAME/KEY: Modified-site
            (B) LOCATION: 26
            (D) OTHER INFORMATION: Xaa= basic amino acid;

(ix) FEATURE:
            (A) NAME/KEY: Modified-site
            (B) LOCATION: 27
            (D) OTHER INFORMATION: Xaa= non-charged hydrophilic amino
                acid, basic amino acid;

(ix) FEATURE:
            (A) NAME/KEY: Modified-site
            (B) LOCATION: 30
            (D) OTHER INFORMATION: Xaa= acidic amino acid, aliphatic
                neutral amino acid;

(xi) SEQUENCE DESCRIPTION: SEQ ID NO:35:

Ser Val Ser Glu Ile Gln Leu Met His Xaa Xaa Xaa Xaa Xaa Xaa Xaa
1               5                   10                  15

Xaa Met Xaa Arg Xaa Glu Trp Leu Arg Xaa Xaa Leu Gln Xaa Val His
            20                  25                  30

Asn Phe Val Ala Leu Gly Ala Pro
            35                  40

(2) INFORMATION FOR SEQ ID NO:36:

(i) SEQUENCE CHARACTERISTICS:
            (A) LENGTH: 84 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 10
            (D) OTHER INFORMATION: Xaa=acidic amino acid;

(ix) FEATURE:
            (A) NAME/KEY: Modified-site
            (B) LOCATION: 11
            (D) OTHER INFORMATION: Xaa=hydrophobic alpha amino acid,
                basic amino acid;

(ix) FEATURE:
            (A) NAME/KEY: Modified-site
            (B) LOCATION: 12
            (D) OTHER INFORMATION: Xaa=Gly, Ala, Ser, Lys, Orn;

(ix) FEATURE:
            (A) NAME/KEY: Modified-site
            (B) LOCATION: 13
            (D) OTHER INFORMATION: Xaa= basic amino acid;

(ix) FEATURE:
            (A) NAME/KEY: Modified-site
            (B) LOCATION: 14
            (D) OTHER INFORMATION: Xaa= basic amino acid;

(ix) FEATURE:
            (A) NAME/KEY: Modified-site
            (B) LOCATION: 15
            (D) OTHER INFORMATION: Xaa= aliphatic neutral amino acid,
                basic amino acid;

(ix) FEATURE:
            (A) NAME/KEY: Modified-site
            (B) LOCATION: 16,17
            (D) OTHER INFORMATION: Xaa= non-charged hydrophilic amino
                acid-basic amino acid;

(ix) FEATURE:
            (A) NAME/KEY: Modified-site
            (B) LOCATION: 19
            (D) OTHER INFORMATION: Xaa= acidic amino acid, basic amino
                acid;

(ix) FEATURE:
            (A) NAME/KEY: Modified-site
            (B) LOCATION: 21
            (D) OTHER INFORMATION: Xaa= aliphatic neutral amino acid,
                basic amino acid;

(ix) FEATURE:
            (A) NAME/KEY: Modified-site
            (B) LOCATION: 26
            (D) OTHER INFORMATION: Xaa= basic amino acid;

(ix) FEATURE:
            (A) NAME/KEY: Modified-site
            (B) LOCATION: 27
            (D) OTHER INFORMATION: Xaa= non-charged hydrophilic amino
                acid, basic amino acid;

(ix) FEATURE:
            (A) NAME/KEY: Modified-site
            (B) LOCATION: 30
            (D) OTHER INFORMATION: Xaa= acidic amino acid, aliphatic
                neutral amino acid;

(xi) SEQUENCE DESCRIPTION: SEQ ID NO:36:

Ser Val Ser Glu Ile Gln Leu Met His Xaa Xaa Xaa Xaa Xaa Xaa
1               5                   10                  15

Xaa Met Xaa Arg Xaa Glu Trp Leu Arg Xaa Xaa Leu Gln Xaa Val His
            20                  25                  30

Asn Phe Val Ala Leu Gly Ala Pro Leu Ala Pro Arg Asp Ala Gly Ser

-continued

```
              35                      40                      45
Gln Arg Pro Arg Lys Lys Glu Asp Asn Val Leu Val Glu Ser His Glu
            50                      55                      60
Lys Ser Leu Gly Glu Ala Asp Lys Ala Asp Val Asn Val Leu Thr Lys
65                      70                      75                      80
Ala Lys Ser Gln
```

PARATHYROID HORMONE DERIVATIVES AND THEIR USE

This application is a divisional of 08/662871, filed Jun. 12, 1996, now abandoned.

FIELD OF THE INVENTION

The present invention relates to novel derivatives of parathyroid hormone and use thereof.

BACKGROUND OF THE INVENTION

Parathyroid hormone (PTH) is produced in the parathyroid, and plays an important role, acting on the bone and the kidney which are its target organs to control the blood calcium and phosphate ion levels. PTH is a peptide hormone composed of 84 amino acids, and its biological activity is known to be able to be reproduced by the N-terminal (the 1 to 34-positions) peptide fragment [G. W. Tregear et al., *Endocrinology*, 93, 1349–1353 (1973)].

This N-terminal (the 1 to 34-positions) peptide fragment of human PTH (hereinafter briefly referred to as "human PTH(1–34)") has the following amino acid sequence:

```
1 2 3 4 5 6 7 8 9 10 11 12 H-Ser-Val-Ser-Glu-Ile-Gln-Leu-Met-
   His-Asn-Leu-Gly-13 14 15 16 17 18 19 20 21- 22 23 24 25 26
   Lys-His-Leu-Asn-Ser-Met-Glu-Arg-Val-Glu-Trp-Leu-Arg-Lys-
   27 28 29 30 31 32 33 34 Lys-Leu-Gln-Asp-Val-His-Asn-Phe-
   OH                                              (SEQ ID NO: 1)
```

In order to understand the structure-activity relationship of said hormone, various derivatives of the PTH(1–34) fragment have been synthesized. Previously, investigations of bovine PTH(1–34) have been mainly conducted. However, recent investigations are increasingly directed to human PTH(1–34). For example, conversion of the C-terminal Phe of human PTH(1–34) to Phe-NH$_2$ is known to cause a rise in activity [JP-A-58-96052 (the term "JP-A" as used herein means an "unexamined published Japanese patent application")]. However, this is considered that decomposition caused by carboxypeptidase is inhibited, resulting in an apparent rise in activity. For a molecule in which 2 Met residues contained in human PTH(1–34) are substituted by Nle residues, hormone activity is known to be prevented from disappearance by oxidation (JP-A-61-24598).

F. E. Cohen et al. [*The Journal of Biological Chemistry*, 226, 1997–2004 (1991); WO 92/00753] substituted various L-amino acids for Ser at the 3-position in human PTH(1–34) and bovine PTH(1–34). As a result, Ala-substituted derivatives showed activity approximately equivalent to that of the natural type fragments, but derivatives substituted by the other amino acids are extremely lowered in activity. Further, substitution of amino acids at the 6- and 9-positions does not provide derivatives having activity suitable for use as medical drugs. Furthermore, Wo 93/06845 discloses that even when the sequence of the consecutive basic amino acids of the 25- to 27-positions of PTH(1–34) is substituted by another amino acid sequence, its biological activity is retained, but activity on blood pressure or on smooth muscle is decreased. WO 93/06846 also discloses that an analogue in which the 23-position is substituted by another amino acid has a similar effect. In addition, JP-A-6-184198 (WO 94/02510) discloses various analogues substituted by amino acid, as well as analogues in which amino groups of side chains are modified.

From biological activity of PTH, it is expected that PTH can be used as drugs useful for various bone diseases, etc. However, the following properties of the peptide make this difficult.

(1) PTH is easily decomposed by various enzymes in the body;

(2) The absorption efficiency of PTH into the body by various routes is very low; and (3) PTH is unstable under various physical and chemical conditions such as oxidation.

In order to solve such problems, and to elucidate the structure-activity relationship of said hormone, various derivatives of the PTH(1–34) active fragment have been synthesized. On measurement of biological activity of these compounds, compounds avoiding any of the problems of the above (1) to (3) have enhanced activity in some cases as described above with respect to the derivative having Phe-NH$_2$ at the 34-position. Derivatives enhanced in inherent activity, for example, by an increase in affinity or receptors can compensate for the problems of the above (1) to (3) by their high activity.

Previously, the present inventors made substitution of amino acids of human PTH(1–34) by chemical synthesis and have discovered that this object were attained by (1) subjecting any of the amino acids at the 1-, 8-, 11-, 12-, 13-, 18-, 19-, 21- 23-, 25-, 26-, 27- and 34-positions of human PTH(1–34) to amino acid substitution considering the resistance to various proteases, (2) enhancing activity of said hormone by amino acid substitution considering two-dimensional structure to be expected, hydrophilicity, hydrophobicity or ionic environment, or (3) substituting amino acids unstable to acidic or alkaline conditions, oxidation conditions, etc. by amino acids stable to these conditions without reducing activity, and have provided excellent human PTH(1–34) derivatives (JP-A-5-32696). Further, the present inventors discovered that derivatives of said peptide obtained by substitution of any of the amino acids at the 3-, 14-, 15-, 16-, 17-, 25-, 26-, 27- and 34-positions of the human PTH(1–34) sequence, or a combination thereof have excellent activity (JP-A-5-320193).

Furthermore, the present inventors discovered that a peptide derivative in which any of the amino acids at the 34- to 47-positions of human PTH(1–84) is substituted by Cys can form a dimer, and that introduction of another functional group can convert the peptide to a compound having more desirable properties (JP-A-5-271279).

SUMMARY OF THE INVENTION

It is therefore an object of the present invention to provide human PTH(1–34) derivatives having improved characteristics.

The present inventors have discovered that substitution for amino acid Asn at the 10-position of human PTH(1–34) by an acidic amino acid leads to derivatives having improved characteristics. Further, the present inventors have succeeded in discovering compounds having improved characteristics by combining this finding with the results of the present inventors' prior inventions described above, thus completing the present invention.

The present invention provides a peptide having the following amino acid sequence or a salt thereof:

Ser-Val-Ser-Glu-Ile-Gln-Leu-Met-His-R$_1$-R$_2$-R$_3$-R$_4$-R$_5$-R$_6$-R$_7$-Met-R$_8$-Arg-R$_9$-Glu-Trp-Leu-Arg-R$_{10}$-R$_{11}$-Leu-Gln-R$_{12}$-Val-His-Asn-R$_{13}$ (SEQ ID NO: 2)

wherein R$_1$ represents an acidic amino acid; R$_2$ represents a hydrophobic α-amino acid or a basic amino acid; R$_3$ represents Gly, or D- or L-Ala, Ser, Lys, Orn or Trp; R$_4$ represents a basic amino acid; R$_5$ represents a basic amino acid; $R_6$ represents an aliphatic neutral amino acid or a basic amino acid; $R_7$ represents a dipeptide consisting of non-charged hydrophilic amino acids, basic amino acids or a combination thereof; $R_8$ represents an acidic amino acid or a basic amino acid; $R_9$ represents an aliphatic neutral amino acid or a basic amino acid; $R_{10}$ represents a basic amino acid; $R_{11}$ represents a non-charged hydrophilic amino acid or a basic amino acid; $R_{12}$ represents an acidic amino acid or an aliphatic neutral amino acid; and $R_{13}$ represents an aromatic amino acid, or a peptide corresponding to human PTH(34–35), (34–36), (34–37), (34–38), (34–39) or (34–40), or a peptide corresponding to human PTH(34–84) in which at least one of the amino acids between the 35-position and the 45-position may be substituted by D- or L-Cys, wherein the carboxyl group of said aromatic amino acid or the C-terminal amino acid of said peptides may be amidated.

The present invention further provides a pharmaceutical composition comprising the above-mentioned peptide or salt thereof, and particularly a bone disease preventive-therapeutic agent comprising the above-mentioned peptide or salt thereof.

DESCRIPTION OF THE PREFERRED EMBODIMENTS $R_1$ to $R_{13}$ defined above are further described in detail.

The acidic amino acids represented by $R_1$ may be either natural amino acids or non-natural amino acids, as long as they are acidic amino acids. In particular, such acidic amino acids include amino acids represented by the following formula:

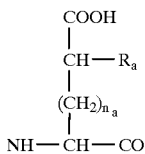

wherein $R_a$ represents H, OH or COOH; and $n_a$ represents an integer of 0 to 4.

The hydrophobic α-amino acids represented by $R_2$ include amino acids which are not protein-constituting ones such as Nle (norleucine), naphthylalanine and 4-chlorophenylalanine, as well as protein-constituting amino acids having alkyl groups which may be substituted at side chains thereof such as Ala, Val, Leu, Ile, Pro and Met, and aromatic amino acids such as Phe, Trp and Tyr.

The basic amino acids represented by $R_2$ may be either natural amino acids or non-natural amino acids, as long as they are basic amino acids, and particularly include basic amino acids represented by the following formula:

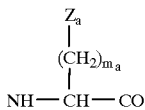

wherein $Z_a$ represents $NH_2$, $NHC(NH)NH_2$ or an imidazolyl group; and $m_a$ represents an integer of 1 to 5.

$R_3$ represents Gly, or D- or L-Ala, Ser, Lys, Orn or Trp.

The basic amino acids represented by $R_4$ may be either natural amino acids or non-natural amino acids, as long as they are basic amino acids, and particularly include basic amino acids represented by the following formula:

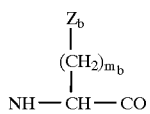

wherein $Z_b$ represents $NH_2$, $NHC(NH)NH_2$ or an imidazolyl group; and $m_b$ represents an integer of 1 to 5.

The basic amino acids represented by $R_5$ may be either natural amino acids or non-natural amino acids, as long as they are basic amino acids, and particularly include basic amino acids represented by the following formula:

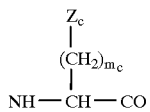

wherein $Z_c$ represents $NH_2$, $NHC(NH)NH_2$ or an imidazolyl group; and $m_c$ represents an integer of 1 to 5.

The aliphatic neutral amino acids represented by $R_6$ may be either natural amino acids or non-natural amino acids, as long as they are aliphatic neutral amino acids, and particularly include aliphatic neutral amino acids represented by the following formula:

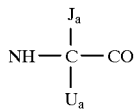

wherein $J_a$ and $U_a$ each represent H or an alkyl group having 1 to 4 carbon atoms.

Further, $R_6$ may also be a basic amino acid. In that case, the basic amino acids represented by $R_6$ may be either natural amino acids or non-natural amino acids, as long as they are basic amino acids, and particularly include basic amino acids represented by the following formula:

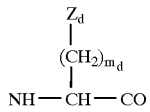

wherein $Z_d$ represents $NH_2$, $NHC(NH)NH_2$ or an imidazolyl group; and $m_d$ represents an integer of 1 to 5.

Examples of the non-charged hydrophilic amino acids constituting the dipeptides represented by $R_7$ include (1) Gly and (2) L- or D-Ser, Thr, Cys, Asn or Gln, and (3) the basic amino acids constituting the dipeptides represented by $R_7$ may be either natural amino acids or non-natural amino acids, as long as they are basic amino acids. In particular, such basic amino acids include basic amino acids represented by the following formula:

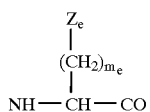

wherein $Z_e$ represents $NH_2$, $NHC(NH)NH_2$ or an imidazolyl group; and $m_e$ represents an integer of 1 to 5.

In addition to the above (1), (2) and (3), the peptides represented by $R_7$ include dipeptides consisting of (4) a combination thereof.

The acidic amino acids represented by $R_8$ may be either natural amino acids or non-natural amino acids, as long as they are acidic amino acids, and particularly include amino acids represented by the following formula:

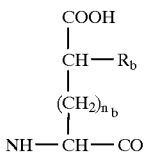

wherein $R_b$ represents H, OH or COOH; and $n_b$ represents an integer of 0 to 4.

Further, the basic amino acids represented by $R_8$ may be either natural amino acids or non-natural amino acids, as long as they are basic amino acids, and particularly include basic amino acids represented by the following formula:

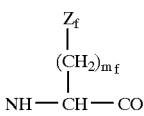

wherein $Z_f$ represents $NH_2$, $NHC(NH)NH_2$ or an imidazolyl group; and $m_f$ represents an integer of 1 to 5.

The aliphatic neutral amino acids represented by $R_9$ may be either natural amino acids or non-natural amino acids, as long as they are aliphatic neutral amino acids, and particularly include aliphatic neutral amino acids represented by the following formula:

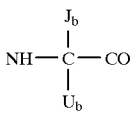

wherein $J_b$ and $U_b$ each represent H or an alkyl group having 1 to 4 carbon atoms.

Further, the basic amino acids represented by $R_9$ may be either natural amino acids or non-natural amino acids, as long as they are basic amino acids, and particularly include basic amino acids represented by the following formula:

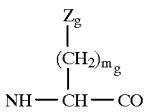

wherein $Z_g$ represents $NH_2$, $NHC(NH)NH_2$ or an imidazolyl group; and $m_g$ represents an integer of 1 to 5.

The basic amino acids represented by $R_{10}$ may be either natural amino acids or non-natural amino acids, as long as they are basic amino acids, and particularly include basic amino acids represented by the following formula:

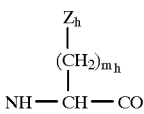

wherein $Z_h$ represents $NH_2$, $NHC(NH)NH_2$ or an imidazolyl group; and $m_h$ represents an integer of 1 to 5.

Examples of the non-charged hydrophilic amino acids represented by $R_{11}$ include (1) Gly and (2) L- or D-Ser, Thr, Cys, Asn or Gln, and (3) the basic amino acids represented by $R_{11}$ may be either natural amino acids or non-natural amino acids, as long as they are basic amino acids. In particular, such basic amino acids include basic amino acids represented by the following formula:

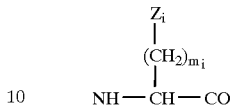

wherein $Z_i$ represents $NH_2$, $NHC(NH)N_2$ or an imidazolyl group; and $m_i$ represents an integer of 1 to 5.

The acidic amino acids represented by $R_{12}$ may be either natural amino acids or non-natural amino acids, as long as they are acidic amino acids, and particularly include amino acids represented by the following formula:

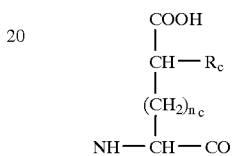

wherein $R_c$ represents H, OH or COOH; and $n_c$ represents an integer of 0 to 4.

Further, $R_{12}$ may also be an aliphatic neutral amino acid. The aliphatic neutral amino acids represented by $R_{12}$ may be either natural amino acids or non-natural amino acids, as long as they are aliphatic neutral amino acids, and particularly include aliphatic neutral amino acids represented by the following formula:

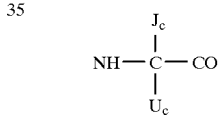

wherein $J_c$ and $U_c$ each represent H or an alkyl group having 1 to 4 carbon atoms.

$R_{13}$ includes Phe, Tyr, Phe-Val, Phe-Val-Ala, Phe-Val-Ala-Leu (SEQ ID NO: 3), Phe-Val-Ala-Leu-Gly (SEQ ID NO: 4), Phe-Val-Ala-Leu-Gly-Ala (SEQ ID NO: 5) and Phe-Val-Ala-Leu-Gly-Ala-Pro (SEQ ID NO: 6) or Phe-Val-Ala-Leu-Gly-Ala-Pro-Leu-Ala-Pro-Arg-Asp-Ala-Gly-Ser-Gln-Arg-Pro-Arg-Lys-Lys-Glu-Asp-Asn-Val-Leu-Val-Glu-Ser-His-Glu-Lys-Ser-Leu-Gly-Glu-Ala-Asp-Lys-Ala-Asp-Val-Asn-Val-Leu-Thr-Lys-Ala-Lys-Ser-Gln (SEQ ID NO: 7) in which at least one of the second to twelfth amino acids may be substituted by D- or L-Cys, wherein the carboxyl group of the C-terminal amino acid may be substituted by an amido group or an $N-C_{1-4}$-alkylamido group.

$R_1$ to $R_{13}$ are described in more detail.

Specific examples of $R_1$ include Asp, Glu, aminoadipic acid, aminosuberic acid and 4-carboxyglutamic acid, and Asp and Glu are preferred among others.

Specific examples of $R_2$ include Leu, Phe, Lys and naphthylalanine, and Leu, Phe and Lys are preferred among others.

Specific examples of $R_3$ include Gly, D-Trp, D-Ala and D-Ser, and Gly, D-Ala and D-Ser are preferred among others.

Specific examples of $R_4$ include Lys and Orn.

Specific examples of $R_5$ include His and Lys, and His is preferred among others.

Specific examples of $R_6$ include Leu and Lys, and Leu is preferred among others.

Specific examples of $R_7$ include Asn-Ser, Lys-Lys, Asn-Lys, Lys-Ser and Ser-Ser, and Asn-Ser, Lys-Lys, Lys-Ser and Ser-Ser are preferred among others.

Specific examples and preferred examples of $R_8$ include Glu and Arg.

Specific examples and preferred examples of $R_9$ include Val and Arg.

Specific examples and preferred examples of $R_{10}$ include Lys and Arg.

Specific examples and preferred examples of $R_{11}$ include Lys and Gln.

Specific examples and preferred examples of $R_{12}$ include Asp and 2-aminoisobutyric acid.

Specific examples and preferred examples of $R_{13}$ include Phe.

Examples of the peptides or the salts thereof of the present invention include peptides or salts thereof having the amino acid sequence represented by SEQ ID NO: 2, wherein $R_1$ is Asp, Glu, aminoadipic acid, aminosuberic acid or 4-carboxyglutamic acid; $R_2$ is Leu, Phe, Lys or naphthylalanine; $R_3$ is Gly, D-Trp, D-Ala or D-Ser; $R_4$ is Lys or Orn; $R_5$ is His or Lys; $R_6$ is Leu or Lys; $R_7$ is Asn-Ser, Lys-Lys, Asn-Lys, Lys-Ser or Ser-Ser; $R_8$ is Glu or Arg; $R_9$ is Val or Arg; $R_{10}$ is Lys or Arg; $R_{11}$, is Lys or Gln; $R_{12}$ is Asp or 2-aminoisobutyric acid; and $R_{13}$ is Phe.

Examples of the peptides or the salts thereof of the present invention further include peptides or salts thereof having the amino acid sequence represented by SEQ ID NO: 2, wherein $R_1$ is an acidic amino acid; $R_2$ is a hydrophobic α-amino acid or a basic amino acid; $R_3$ is Gly, or D- or L-Ala, Ser, Lys or Orn; $R_4$ is Lys; $R_5$ is His; $R_6$ is Leu; $R_7$ is a dipeptide consisting of non-charged hydrophilic amino acids, basic amino acids or a combination thereof; $R_8$ is Glu; $R_9$ is Val; $R_{10}$ is Lys; $R_{11}$ is a non-charged hydrophilic amino acid or a basic amino acid; $R_{12}$ is Asp; and $R_{13}$ is an aromatic amino acid, or a peptide corresponding to human PTH(34–35), (34–36), (34–37), (34–38), (34–39) or (34–40), or a peptide corresponding to human PTH(34–84) in which at least one of the amino acids between the 35-position and the 45-position may be substituted by D- or L-Cys, wherein the carboxyl group of said aromatic amino acid or the C-terminal amino acid of each of said peptides may be amidated.

Still further, examples of the peptides or the salts thereof of the present invention include peptides or salts thereof having the amino acid sequence represented by SEQ ID NO: 2, wherein $R_1$ is an acidic amino acid represented by the following formula:

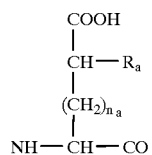

wherein $R_a$ represents H, OH or COOH; and $n_a$ represents an integer of 0 to 4; $R_2$ is Ala, Val, Leu, Ile, Pro, Met, Phe, Trp, Tyr, Nle, naphthylalanine, 4-chlorophenylalanine or a basic amino acid represented by the following formula:

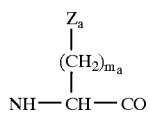

wherein $Z_a$ represents $NH_2$, $NHC(NH)NH_2$ or an imidazolyl group; and $m_a$ represents an integer of 1 to 5; $R_3$ is Gly, or D- or L-Ala, Ser, Lys or Orn; $R_4$ is Lys; $R_5$ is His; $R_6$ is Leu; $R_7$ is a dipeptide consisting of (1) Gly, (2) L- or D-Ser, Thr, Cys, Asn or Gln, (3) basic amino acids represented by the following formula:

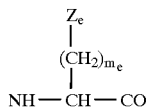

wherein $Z_e$ represents $NH_2$, $NHC(NH)NH_2$ or an imidazolyl group, and $m_e$ represents an integer of 1 to 5; or (4) a combination thereof; $R_8$ is Glu; $R_9$ is Val; $R_{10}$ is Lys; $R_{11}$ is (1) Gly, (2) L- or D-Ser, Thr, Cys, Asn or Gln, or (3) a basic amino acid represented by the following formula:

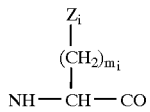

wherein $Z_i$ represents $NH_2$, $NHC(NH)NH_2$ or an imidazolyl group, and $m_i$ represents an integer of 1 to 5; $R_{12}$ is Asp; and $R_{13}$ is Phe, Tyr, Phe-Val, Phe-Val-Ala, Phe-Val-Ala-Leu (SEQ ID NO: 3), Phe-Val-Ala-Leu-Gly (SEQ ID NO: 4), Phe-Val-Ala-Leu-Gly-Ala (SEQ ID NO: 5) and Phe-Val-Ala-Leu-Gly-Ala-Pro (SEQ ID NO: 6) or Phe-Val-Ala-Leu-Gly-Ala-Pro-Leu-Ala-Pro-Arg-Asp-Ala-Gly-Ser-Gln-Arg-Pro-Arg-Lys-Lys-Glu-Asp-Asn-Val-Leu-Val-Glu-Ser-His-Glu-Lys-Ser-Leu-Gly-Glu-Ala-Asp-Lys-Ala-Asp-Val-Asn-Val-Leu-Thr-Lys-Ala-Lys-Ser-Gln (SEQ ID NO: 7) in which at least one of the second to twelfth amino acids may be substituted by D- or L-Cys, wherein the carboxyl group of the C-terminal amino acid may be substituted by an amido group or an N-$C_{1-4}$-alkylamido group. In particular, preferred examples thereof include peptides or salts thereof, wherein $R_1$ is Asp, Glu, aminoadipic acid, aminosuberic acid or 4-carboxyglutamic acid. The amidated carboxyl groups include, for example, amido groups and N-$C_{1-4}$-alkylamido groups, and the N-$C_{1-4}$-alkylamido groups include, for example, methylamido, ethylamido, propylamido and butylamido.

The alkyl groups having 1 to 4 carbon atoms represented by Ja, Jb, Jc, Ua, Ub and Uc include for example methyl, ethyl, n-propyl, isopropyl, n-butyl, isobutyl and sec-butyl.

The compound of the present invention can be substituted not only at one position, but also at several positions in combination. In particular, a combination of substitutions at 4 or less positions is preferable.

Examples thereof include [Asp$^{10}$, Lys$^{11}$] hPTH(1–34), [Asp$^{10}$] hPTH(1–34), [Glu$^{10}$] hPTH(1–34), [Asp$^{10}$, Phe$^{11}$] hPTH(1–34), [Asp$^{10}$, Ala(2-Naph)$^{11}$] hPTH(1–34), [Glu$^{10}$] hPTH(1–34) methylamide, [Glu$^{10}$, Lys$^{16,17}$] hPTH(1–34), [Glu$^{10}$, Ser$^{16}$] hPTH(1–34), [Glu$^{10}$, Tyr$^{34}$] hPTH(1–34), [Glu$^{10}$, Cys$^{35}$] hPTH(1–84), [Glu$^{10}$, D-Ala$^{12}$] hPTH(1–34), [Glu$^{10}$, Lys$^{16,17}$, Gln$^{27}$] hPTH(1–34), [Glu$^{10}$, Phe$^{11}$, Lys$^{16}$, Gln$^{27}$] hPTH(1–34). [Glu$^{10}$, Orn$^{13}$] hPTH(1–34), [Glu$^{10}$, Phe$^{11}$, D-Ala$^{12}$] hPTH(1–34) and [Glu$^{10}$] hPTH(1–84).

Preferred examples thereof include [Asp$^{10}$, Lys$^{11}$] hPTH (1–34), [Glu$^{10}$] hPTH(1–34), [Glu$^{10}$, Phe$^{11}$, Lys$^{16}$, Gln$^{27}$] hPTH(1–34), [Glu$^{10}$, Ser$^{16}$] hPTH(1–34), [Glu$^{10}$, Orn$^{13}$] hPTH(1–34), [Glu$^{10}$, Phe$^{11}$, D-Ala$^{12}$] hPTH(1–34), [Asp$^{10}$, Phe$^{11}$] hPTH(1–34) and [Asp$^{10}$] hPTH(1–34) among others.

The peptide compounds of the present invention can be synthesized by gene recombination or chemical synthesis. Especially, the latter can be carried out mainly using an automatic peptide synthesizer.

The production of the peptides according to gene recombination is described in Japanese Patent Unexamined Publication Nos. 5-320193, 5-271279 and 5-304976, which is briefly illustrated below.

In order to produce the parathyroid hormone derivative of the present invention by gene recombination, a gene coding for the amino acid sequence of human PTH(1–84) (for example, European Patent Publication No. 483509) or a gene coding for an amino acid sequence corresponding to a C-terminal deletion form thereof is converted to a gene coding for a target derivative by conventional DNA techniques, for example, site-directed mutagenesis. Site-directed mutagenesis is well known and described in R. F. Lather and J. P. Lecoq, *Genetic Engineering*, pp.31–50, Academic Press (1983). Mutagenesis directed to oligonucleotides is described in M. Smith and S. Gillam, *Genetic Engineering: Principles and Methods*, vol.3, pp. –32, Plenum Press (1981).

In order to produce structural genes coding for the amino acid-substituted parathyroid hormone derivatives of the present invention having various chain lengths, for example, (a) single stranded DNA comprising a single strand of a structural gene of human PTH or a C-terminal deletion form thereof is hybridized with a mutant oligonucleotide primer, (b) the primer is extended with DNA polymerase to form a mutational heteroduplex, and subsequently, (c) the mutational heteroduplex is duplicated.

Following the duplication, a mutant gene is isolated from progeny of a mutant chain and inserted into an appropriate vector, which is used for transformation of an appropriate host organism or cell.

Then, a phage DNA transferring the mutagenized gene is isolated and introduced into a plasmid.

The gene thus cloned is ligated downstream from a promoter in a vehicle (vector) suitable for expression, whereby an expression vector can be obtained.

Examples of the vectors include *E. coli*-derived plasmids (for example, pBR322, pBR325, pUC12 and pUC13), *Bacillus subtilis*-derived plasmids (for example, pUB110, pTP5 and pC194), yeast-derived plasmids (for example, pSH19 and pSH15), bacteriophages such as λ phage, and animal viruses such as retroviruses and vaccinia viruses.

The gene may have ATG as a translation initiation codon at the 5'-terminus thereof, and TAA, TGA or TAG as a translation termination codon at the 3'-terminus thereof. A promoter is further ligated upstream therefrom and operably linked thereto to express the gene. The promoter used in this invention may be any as long as it is suitable for expression in a host selected for the gene expression.

Using the vector thus constructed, which contains recombinant DNA having a nucleotide sequence coding for the parathyroid hormone derivative of the present invention, a transformant for carrying said vector is prepared. The host cells include Escherichia, Bacillus, yeast and animal cells.

The resulting transformant carrying the vector containing the recombinant DNA having the nucleotide sequence coding for the parathyroid hormone derivative is cultivated in a medium, thereby producing the parathyroid hormone derivative.

The parathyroid hormone derivative can be isolated and purified from the above-mentioned culture product, for example, by the following method.

The cultured cells are first disrupted by a French press, ultrasonic treatment, lysozyme, freeze-thawing, glass beads, etc to extract the contents. When the cells are disrupted, 1–8M urea or 1–6M guanidine hydrochloride may be added to a buffer solution. Addition of a reducing agent such as dithiothreitol increases the recovery of the target parathyroid hormone derivative in some cases. The reducing agent is added after lysozyme has been allowed to act on.

Then, the resulting cell extract is separated into a supernatant and a precipitate by centrifugation. When the parathyroid hormone derivative is recovered in the supernatant, it can be effectively purified, for example, by a method similar to the method described in M. Iwane, *Biochem. Biophys. Res. Commun.*, 146, 470–477 (1987). When the parathyroid hormone derivative is recovered in the precipitate, the precipitate is dissolved into a solution containing a protein denaturant such as guanidine hydrochloride or urea, and then, the concentration of the protein denaturant is reduced by dialysis or dilution, whereby the parathyroid hormone derivative having biological activity can be obtained. The parathyroid hormone derivative recovered from the precipitate is purified if necessary to give a product of high purity and high activity similarly to the precipitate recovered from the supernatant.

Further separating and purifying means include column chromatography and high performance liquid chromatography such as gel filtration, ion-exchange chromatography using cation exchange resins or anion exchange resins, hydrophobic chromatography and partition adsorption chromatography.

Basic synthesis using an automatic peptide synthesizer can be performed, for example, based on the method of R. B. Merrifield [*Advances in Enzymology*, 32, 221–296 (1969)]. This method is based on the principle that the carboxyl terminal amino acid is covalently bound to a resin carrier, and removal of an amino-protecting group and condensation of a protected amino acid are in turn repeated to extend a peptide chain to the amino terminus, thereby obtaining a protected peptide resin having a target amino acid sequence. Condensation of each amino acid and removal of the amino-protecting group are conducted under approximately identical conditions, and purification of an intermediate is not carried out. Accordingly, synthesis can be easily carried out. Moreover, this method is rapid and very convenient in synthesizing various peptides. The protected peptide resin thus obtained is reacted with anhydrous hydrogen fluoride, trifluoromethanesulfonic acid or trifluoroacetic acid in the coexistence of various additives, whereby elimination of the peptide from the resin and removal of all the protecting groups can be performed in one step. The conditions of the automatic peptide synthesizer can usually be established according to a protocol thereof.

The resulting crude peptide product can be purified by known means for purifying peptides or proteins. Examples of such means include column chromatography and high performance liquid chromatography based on various principles, such as gel filtration, ion-exchange chromatography using cation exchange resins or anion exchange resins, hydrophobic chromatography and partition adsorption chromatography.

The peptides of the present invention can be obtained in the form of various salts. As the salts, physiologically acceptable salts or salts available as raw materials are used. Examples thereof include salts of inorganic acids and organic acids such as formic acid, acetic acid, tartaric acid and citric acid, inorganic bases such as sodium and ammonium, and organic bases such as triethylamine, ethylamine and methylamine.

When the target product is obtained in the free state, it may be normally converted to a salt thereof. When the target product is obtained as the salt, it can also be normally converted to a free form or another salt.

The human PTH(1–34) derivative peptides represented by the general formula of the present invention are low in toxicity and are safe, so that they can be used as drugs alone or in combination with excipients. In particular, they can be used as preventive or therapeutic agents for bone diseases (osteogenic diseases), therapeutic agents for hypoparathyroidism, therapeutic agents for hypertension and therapeutic agents for climacteric disturbance (including climacterium-like disturbance by use of other drugs). Prevention and therapy of bone diseases include all prevention and therapy of bone diseases such as improvements in bone formation, namely fixing of calcium in the bone, and prevention and therapy of osteoporosis due to various causes (for example, juvenilis, menopause, postmenopause, posttrauma, aging, estrogen deficiency, growth hormone deficiency, hypothyroidism, hyperthyroidism, nutritional or metabolic anomaly, corticosteroid therapy and inactivity), acute and chronic bone disorders associated with bone fracture or demineralization of the skeleton, osteohalisteresis, osteozemia of the periodontal ligament, osteozemia caused by arthritis or arthrosteitis, and therapy of hypoparathyroidism.

The forms thereof include injections, nasotracheal absorption agents, perrectum absorption agents, transvaginal absorption agents and percutaneous absorption agents. In some cases, they are orally administered.

When the peptides are used as such therapeutic agents, effective amounts thereof are dosed to mammals (for example, humans, mice, rats, dogs, cats, cattle, pigs, monkeys, etc.). Although they are generally used within the range of 1 ng to 100 μg/kg of weight, preferably 5 μg to 100 μg/kg of weight, precise amounts thereof may be determined by those skilled in the art.

When the peptides are used as the preventive or therapeutic agents, they must be carefully purified so as to contain no bacteria and no pyrogens. Such purification may be performed according to methods known in the art.

The peptides, when used as the preventive or therapeutic agents for osteoporosis and the like, can be administered parenterally in the form of the above-mentioned injections, nasotracheal absorption agents, perrectum absorption agents, transvaginal absorption agents or percutaneous absorption agents, alone or in combination with pharmaceutically acceptable carriers, excipients or diluents. The injections include subcutaneous injections, intracutaneous injections, intramuscular injections and drip injections. Such injections are prepared by methods known in the art, namely by dissolving, suspending or emulsifying the compounds of the present invention in sterile aqueous solutions or oily solutions. The aqueous solutions for injection include physiological saline and isotonic solutions containing glucose or other adjuvants (for example, D-sorbitol, D-mannitol and sodium chloride), and may be used in combination with appropriate solubilizing adjuvants such as alcohols (for example, ethanol), polyalcohols (for example, polypropylene glycol and polyethylene glycol) and nonionic surface active agents (for example, Polysolvate 80 and HCO-50). The oily solutions include sesame oil and soybean oil, and may be used in combination with solubilizing adjuvants such as benzyl benzoate, benzyl alcohol, etc. The preparations may further contain buffers (for example, phosphate buffer and sodium acetate buffer), soothing agents (for example, benzalkonium chloride and procaine hydrochloride), stabilizing agents (for example, human serum albumin and polyethylene glycol), preservatives (for example, benzyl alcohol and phenol), etc. The injections thus prepared are usually filled into appropriate ampuls. The peptides of the present invention are orally administered in some cases. When oral preparations such as powders, tablets, granules and capsules are produced, pharmaceutically acceptable carriers can be incorporated. The carriers include excipients (for example, lactose and starch), lubricants (for example, magnesium stearate and talc), binders (for example, hydroxypropyl cellulose, hydroxypropylmethyl cellulose and macrogol) and disintegrators (for example, starch, and calcium carboxymethyl cellulose). Further, additives such as preservatives (for example, benzyl alcohol, chlorobutanol, methyl paraoxybenzoate and propyl paraoxybenzoate), antioxidants, coloring agents and flavoring agents can be used if necessary. In the case of the injections, it is suitable that the peptides of the present invention are given in a dose of 50 ng to 5 mg, and preferably 20 μg to 300 μg, once a day to once for every 3 days, for adults. The concentration of the peptides of the present invention is suitably 10 μg to 100 μg/ml for the injections. When the preparations are used as percutaneous absorption agents, they can be absorbed through the skin by iontophoresis. It is suitable that they are given in a dose of 50 ng to 5 mg, preferably 20 μg to 1 mg, and more preferably 20 μg to 400 μg, once a day to once for every 3 days.

When amino acids and the like are indicated by abbreviations in this specification, the abbreviations adopted by the IUPAC-IUB Commission on Biochemical Nomenclature or those commonly used in the art are employed. For example, the following abbreviations are used. When the amino acids are capable of existing as optical isomers, it is understood that the L-forms are represented unless otherwise specified.

Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Asp or D: Aspartic acid
Lys or K: Lysine
Arg or R: Arginine
His or H: Histidine
Phe or F: Phenylalanine
Tyr or Y: Tyrosine
Trp or W: Tryptophan
Pro or P: Proline
Asn or N: Asparagine
Gln or Q: Glutamine
Nle: Norleucine
Orn: Ornithine
Gla: 4-Carboxyglutamic acid
Ala(2-Naph): 2-Naphthylalanine
Aad: 2-Aminoadipic acid
Asu: 2-Aminosuberic acid
Aib: 2-Aminoisobutyric acid;
hPTH: Human PTH The amino acid substitution of the PTH(1–34) as described above provides derivatives exhibiting high PTH activity. First, the amino acid at the 10-position is substituted by an acidic amino acid, whereby an increase in activity is observed. This activity is retained or enhanced in combination with further substitutions at the 11-, 13-, 14-, 15-, 16-, 17-, 19-, 21-, 26-, 27- and 30- positions. The substitution by a D-amino acid at the 12-position increases the resistance to various proteases and provides the persistence of the activity in blood.

The present invention will hereinafter be illustrated in detail with the following examples. It is understood of course that the typical examples of amino acid substitutions described herein are not intended to limit the scope of the invention.

EXAMPLE 1

Synthesis and Purification of PTH (1–34) Peptide Derivatives

The peptides were synthesized in accordance with a modified method of the solid phase peptide synthesis developed by R. B. Merrifield et al., *Adv. Enzymol.* 32, 221–296 (1969), and an automatic peptide synthesizer 430A (Applied Biosystems) was used. A protected peptide-resin was synthesized using the protocol specified by Applied Biosystems. When a derivative having a free carboxylic acid as the carboxyl terminus was desired, a protected amino acid-p-oxymethylphenylacetoamidomethyl resin (polystyrene-1% divinylbenzene) was used as a starting material. When a carboxylamide derivative was desired, a 4-methylbenzhydryl resin was used as a starting material. When, protected amino acids were condensed thereto successively. In order to protect an α-amino group of each amino acid in condensation, a tertiary butoxycarbonyl (BOC) group was used. Side functional groups were protected in the following manner. Hydroxyl groups of serine and threonine were protected as O-benzyl ethers, a hydroxyl group of tyrosine as a p-bromobenzyloxycarbonyl ester, carboxyl groups of glutamic acid and aspartic acid as benzyl esters, imidazole nitrogen of histidine with benzyloxymethyl, a side chain amino group of lysine with 2-chlorobenzyloxycarbonyl, a side chain amino group of ornithine with benzyloxycarbonyl, a guanidine functional group of arginine with a p-toluenesulfonyl group, and indoleimine of tryptophan with a formyl group. All the amino acids were obtained from Applied Biosystems Japan, Nova Biochem or Bachem Chemicals.

After all the amino acids were condensed on the resin, the protected peptide resin was taken out of the synthesizer and dried. The peptide resin (1 g) was allowed to react with anhydrous hydrogen fluoride (8 ml) containing p-cresol (1 ml), 1,2-ethanedithiol (1 ml) and 2-mercaptopyridine (100 mg) at 0° C. for 2 hours. After completion of reaction, hydrogen fluoride was removed by distillation and the residue was washed with diethyl ether to remove most of the mixed reagents. The peptide was extracted with 3% acetic acid (10 ml), and the resin was removed by filtration. The filtrate was purified by gel filtration using Sephadex G-25. The conditions of gel filtration were as follows: column size: 2.6×66 cm; detecting wavelength: 280 nm; solvent: 3% acetic acid; flow rate: 30 ml/hour. Fractions containing the peptide were collected and then lyophilized. The resulting powder sample was further purified by reversed phase high performance liquid chromatography (HPLC) [column: YMC-pack, R&D D-ODS-5 S-5 120A ODS (20×250 mm); eluting solvent A: 0.1% trifluoroacetic acid-99.9% water; eluting solvent B: 0.1% trifluoroacetic acid-99.9% acetonitrile; linear gradient elution program: 0 minute (80% A +20% B), 30 minutes (50% A+50% B) (another elution program may sometimes be used if necessary); elution rate: 5.0 ml/minute; detecting wavelength: 230 or 280 nm]. Peak fractions containing the target pure product were collected, and passed through a Bio RAD AG1X8 column (acetate form, 2.5×2 cm). The eluate was combined with the washings, and acetonitrile was removed therefrom by distillation, followed by lyophilization.

Automatic peptide synthesis was also conducted by a method using 9-fluorenylmethoxycarbonyl (Fmoc) groups as protective groups for the α-amino groups. In this method, an automatic peptide synthesizer 431A (Applied Biosystems) was used. A protected peptide-resin wag synthesized using the protocol specified by Applied Biosystems.

In order to obtain a derivative having a free carboxylic acid as the carboxyl terminus, a protected amino acid-p-alkoxybenzyl alcohol resin was used as a starting material, and then, protected amino acids were condensed thereto successively. In order to protect an a-amino group of each amino acid in condensation, a 9-fluorenylmethoxycarbonyl (Fmoc) group was used. Side functional groups were protected in the following manner. Hydroxyl groups of serine, threonine and tyrosine were protected as O-tertiary butyl ethers, side chain carboxyl groups as tertiary butyl esters, imidazole nitrogen of histidine with a trityl group, side chain amino groups of lysine, etc. with tertiary butoxycarbonyl groups, and a guanidine functional group of arginine with a 2,2,5,7,8-pentamethylchroman-6-sulfonyl group. The protected amino acid-resin was obtained from Watanabe Kagaku Kogyo, and the amino acids were obtained from Watanabe Kagaku Kogyo, Peptide Laboratories, Applied Biosystems Japan, Nova Biochem or Bachem Chemicals.

After all the amino acids were condensed on the resin and the N-terminal Fmoc group was removed, the protected peptide resin was taken out of the synthesizer and dried. Crystalline phenol (0.375 g), 1,2-ethanedithiol(0.125 ml), thioanisole (0.25 ml), distilled water (0.25 ml) and trifluoroacetic acid (5 ml) were in turn added dropwise to the peptide resin (0.5 g) under ice cooling, and then, the temperature was returned to room temperature, followed by reaction for 2 hours. After completion of reaction, trifluoroacetic acid was removed by distillation and the residue was washed with diethyl ether to remove most of the mixed reagents. The peptide was extracted with 30% acetic acid (7 ml), and the resin was removed by filtration. The filtrate was purified by gel filtration using Sephadex G-25. Gel filtration and subsequent purification by reversed phase HPLC were conducted by methods similar to those described above.

Peptides (1) to (25) thus obtained are as follows:

(1) [$Asp^{10}$, $Lys^{11}$] hPTH(1–34) (SEQ ID NO: 8)

(2) [$Asp^{10}$, $Lys^{11}$D-$Trp^{12}$] hPTH(1–34)

(3) [$Asp^{10}$] hPTH(1–34) (SEQ ID NO: 9)

(4) [$Glu^{10}$] hPTH(1–34) (SEQ ID NO: 10)

(5) [$Asp^{10}$, $Phe^{11}$] hPTH(1–34) (SEQ ID NO: 11)

(6) [$Asp^{10}$, Ala(2-Naph)$^{11}$] hPTH(1–34) (SEQ ID NO: 12)

(7) [$Gla^{10}$] hPTH(1–34) (SEQ ID NO: 13)

(8) [$ASu^{10}$] hPTH(1–34) (SEQ ID NO: 14)

(9) [$Aad^{10}$] hPTH(1–34) (SEQ ID NO: 15)

(10) [$Glu^{10}$, $Phe^{11}$, D-$Ala^{12}$] hPTH(1–34)

(11) [$Glu^{10}$, D-$Ser^{12}$] hPTH(1–34)

(12) [$Glu^{10}$, $Lys^{16,\ 17}$] hPTH(1–34) (SEQ ID NO: 16)

(13) [Glu$^{10}$, Lys$^{17}$] hPTH(1–34) (SEQ ID NO: 17)
(14) [Glu$^{10}$, Lys$^{16}$] hPTH(1–34) (SEQ ID NO: 18)
(15) [Glu$^{10}$, Ser$^{16}$] hPTH(1–34) (SEQ ID NO: 19)
(16) [Glu$^{10}$ Lys$^{16}$, Gln$^{27}$] hPTH(1–34) (SEQ ID NO: 20)
(17) [Glu$^{10}$, Phe$^{11}$, Lys$^{16}$, Gln$^{27}$] hPTH(1–34) (SEQ ID NO: 21)
(18) [Asp$^{10}$, Phe$^{11}$, Lys$^{16}$, Gln$^{27}$, Aib$^{30}$] hPTH(1–34) (SEQ ID NO: 22)
(19) [Asp$^{10}$, Phe$^{11}$, Lys$^{16,17}$, Gln$^{27}$, Aib$^{30}$] hPTH(1–34) (SEQ ID NO: 23)
(20) [Asp$^{10}$, Phe$^{11}$, Lys$^{15,16}$, Gln$^{27}$, Aib$^{30}$] hPTH(1–34) (SEQ ID NO: 24)
(21) [Glu$^{10}$, Lys$^{14}$] hPTH(1–34) (SEQ ID NO: 25)
(22) [Glu$^{10}$, Orn$^{13}$] hPTH(1–34) (SEQ ID NO: 26)
(23) [(Asp$^{10}$, Arg$^{19}$] hPTH(1–34) (SEQ ID NO: 27)
(24) [Asp$^{10}$, Arg$^{21}$] hPTH(1–34) (SEQ ID NO: 28)
(25) [Glu$^{10}$, Arg$^{26}$] hPTH(1–34) (SEQ ID NO: 29)

a, b and c in Table 1 are as follows:

a: Subjected to amino acid analysis, after hydrolysis with 6N hydrochloric acid, in the presence of 4% thioglycolic acid at 110° C. for 24 hours in tubes sealed under reduced pressure. Theoretical values are designated in parentheses.

b: Test compounds (no suffix indicates a carboxylic acid type)

c: Retention time of the derivatives on high performance liquid chromatography

Analysis conditions: an M600E high performance chromatogram (Waters) was used to which a 717 Plus autosampler (Waters) was connected. Column: TMC-Pack R&D R-ODS-5 S-5 120A (4.6×250 mm); eluent A: 0.1% trifluoroacetic acid-99.9% water; eluent B: 0.1% trifluoroacetic acid-99.9% acetonitrile; linear gradient elution program: 0 minute (80% A+20% B), 30 minutes (50% A+50% B); flow rate: 1.0 ml/minute; detecting wavelength: 230 nm.

TABLE 1

| Position in hPTH substitution group | (10) $R_1$ | (11) $R_2$ | (12) $R_3$ | (13) $R_4$ | (14) $R_5$ | (15) $R_6$ | (16–17) $R_7$ | (19) $R_8$ | (21) $R_9$ | (26) $R_{10}$ | (27) $R_{11}$ | (30) $R_{12}$ | (34) $R_{13}$ |
|---|---|---|---|---|---|---|---|---|---|---|---|---|---|
| Natural hPTH(1-34) | Asn | Leu | Gly | Lys | His | Leu | Asn—Ser | Glu | Val | Lys | Lys | Asp | Phe |
| Example (1) | Asp | Lys | | | | | | | | | | | |
| Example (2) | Asp | Lys | D-Trp | | | | | | | | | | |
| Example (3) | Asp | | | | | | | | | | | | |
| Example (4) | Glu | | | | | | | | | | | | |
| Example (5) | Asp | Phe | | | | | | | | | | | |
| Example (6) | Asp | Ala(2-Naph) | | | | | | | | | | | |
| Example (7) | Gla | | | | | | | | | | | | |
| Example (8) | Asu | | | | | | | | | | | | |
| Example (9) | Aad | | | | | | | | | | | | |
| Example (10) | Glu | Phe | D-Ala | | | | | | | | | | |
| Example (11) | Glu | | D-Ser | | | | | | | | | | |
| Example (12) | Glu | | | | | | Lys—Lys | | | | | | |
| Example (13) | Glu | | | | | | Asn—Lys | | | | | | |
| Example (14) | Glu | | | | | | Lys—Ser | | | | | | |
| Example (15) | Glu | | | | | | Ser—Ser | | | | | | |
| Example (16) | Glu | | | | | | Lys—Ser | | | | Gln | | |
| Example (17) | Glu | Phe | | | | | Lys—Ser | | | | Gln | | |
| Example (18) | Asp | Phe | | | | | Lys—Ser | | | | Gln | Aib | |
| Example (19) | Asp | Phe | | | | | Lys—Lys | | | | Gln | Aib | |
| Example (20) | Asp | Phe | | | | Lys | Lys—Ser | | | | Gln | Aib | |
| Example (21) | Glu | | | | Lys | | | | | | | | |
| Example (22) | Glu | | | Orn | | | | | | | | | |
| Example (23) | Asp | | | | | | | Arg | | | | | |
| Example (24) | Asp | | | | | | | | Arg | | | | |
| Example (25) | Glu | | | | | | | | | Arg | | | |

TABLE 2-1

Amino acid Composition of PTH(1-34)derivatives (a)

| | Peptide Derivatives (b) | | | | | |
|---|---|---|---|---|---|---|
| Amino acid | (1) | (2) | (3) | (4) | (5) | (6) |
| Asx | 4.00 (4) | 4.00 (4) | 4.00 (4) | 3.00 (3) | 4.00 (4) | 4.00 (4) |
| Ser | 2.73 (3) | 2.71 (3) | 2.21 (3) | 2.15 (3) | 2.69 (3) | 2.43 (3) |
| Glx | 5.26 (5) | 5.28 (5) | 5.75 (5) | 7.08 (6) | 5.72 (5) | 5.76 (5) |
| Gly | 1.02 (1) | | 1.07 (1) | 0.98 (1) | 0.98 (1) | 1.00 (1) |
| Val | 2.75 (3) | 2.76 (3) | 2.76 (3) | 2.70 (3) | 2.70 (3) | 2.71 (3) |
| Met | 1.99 (2) | 2.00 (2) | 1.79 (2) | 1.74 (2) | 1.80 (2) | 1.79 (2) |
| Ile | 0.94 (1) | 0.91 (1) | 0.81 (1) | 0.78 (1) | 0.81 (1) | 0.83 (1) |
| Leu | 3.99 (4) | 3.97 (4) | 5.04 (5) | 4.99 (5) | 3.99 (4) | 4.02 (4) |
| Phe | 0.98 (1) | 0.99 (1) | 0.94 (1) | 0.95 (1) | 1.94 (2) | 0.96 (1) |
| Lys | 3.89 (4) | 3.92 (4) | 2.93 (3) | 2.89 (3) | 2.91 (3) | 2.96 (3) |
| His | 2.86 (3) | 2.95 (3) | 2.68 (3) | 2.68 (3) | 2.70 (3) | 2.72 (3) |

TABLE 2-1-continued

Amino acid Composition of PTH(1-34)derivatives (a)

| | Peptide Derivatives (b) | | | | | |
|---|---|---|---|---|---|---|
| Amino acid | (1) | (2) | (3) | (4) | (5) | (6) |
| Trp | 0.91 (1) | *1.87 (2) | 0.81 (1) | 0.74 (1) | 0.81 (1) | 0.81 (1) |
| Arg | 1.83 (2) | 1.80 (2) | 1.79 (2) | 1.78 (2) | 1.77 (2) | 1.80 (2) |
| Other Amino Acids | | *One of them is D-Trp | | | | Ala (2-Naph) N.D. |
| HPLC retention time (minutes) (C) | 22.3 | 23.4 | 25.9 | 25.8 | 25.6 | 26.9 |

TABLE 2-2

| Amino acid | (7) | (8) | (9) | (10) | (11) | (12) |
|---|---|---|---|---|---|---|
| Asx | 3.00 (3) | 3.00 (3) | 3.00 (3) | 3.00 (3) | 3.00 (3) | 2.00 (2) |
| Ser | 2.64 (3) | 2.65 (3) | 2.60 (3) | 2.63 (3) | *3.51 (3) | 1.72 (2) |
| Glx | *6.03 (5) | 5.01 (5) | 4.99 (5) | 5.97 (6) | 5.98 (6) | 6.00 (6) |
| Gly | 0.99 (1) | 0.99 (1) | 1.01 (1) | | | 1.01 (1) |
| Val | 2.83 (3) | 2.88 (3) | 2.87 (3) | 2.79 (3) | 2.75 (3) | 2.63 (3) |
| Met | 1.97 (2) | 1.82 (2) | 1.97 (2) | 1.89 (2) | 1.91 (2) | 2.20 (2) |
| Ile | 0.94 (1) | 0.91 (1) | 0.95 (1) | 0.98 (1) | 0.97 (1) | 0.95 (1) |
| Leu | 5.13 (5) | 5.11 (5) | 5.11 (5) | 3.95 (4) | 4.93 (5) | 4.97 (5) |
| Phe | 0.97 (1) | 1.00 (1) | 0.98 (1) | 1.94 (2) | 0.96 (1) | 0.99 (1) |
| Lys | 3.27 (3) | 3.23 (3) | 3.25 (3) | 3.01 (3) | 3.00 (3) | 4.90 (5) |
| His | 2.81 (3) | 2.82 (3) | 2.81 (3) | 2.72 (3) | 2.74 (3) | 2.63 (3) |
| Trp | 0.85 (1) | *0.91 (1) | 0.91 (1) | 0.93 (1) | 0.92 (1) | 0.95 (1) |
| Arg | 1.89 (2) | 1.94 (2) | 1.98 (2) | 1.96 (2) | 1.95 (2) | 1.99 (2) |
| Other Amino Acids | *Gla (1) Eluted at Glx | Asu (1) Eluted between Net Ile | Aad (1) Eluted between Glx Gly | D-Ala 1.02 (1) | *One of them is D-Ser | |
| HPLC retention time (minutes) (C) | 26.3 | 26.0 | 26.0 | 25.9 | 24.9 | 25.7 |

TABLE 2-3

| Amino acid | (13) | (14) | (15) | (16) | (17) |
|---|---|---|---|---|---|
| Asx | 3.00 (3) | 2.00 (2) | 2.00 (2) | 2.00 (2) | 2.00 (2) |
| Ser | 1.75 (2) | 2.60 (3) | 3.53 (4) | 2.34 (3) | 2.34 (3) |
| Glx | 6.06 (6) | 6.03 (6) | 6.00 (6) | 7.02 (7) | 7.05 (7) |
| Gly | 1.02 (1) | 1.02 (1) | 1.02 (1) | 0.98 (1) | 0.98 (1) |
| Val | 2.65 (3) | 2.63 (3) | 2.66 (3) | 2.71 (3) | 2.72 (3) |
| Met | 2.22 (2) | 2.20 (2) | 1.86 (2) | 2.22 (2) | 2.22 (2) |
| Ile | 0.96 (1) | 0.95 (1) | 0.91 (1) | 0.93 (1) | 0.94 (1) |
| Leu | 5.01 (5) | 4.97 (5) | 4.70 (5) | 4.94 (5) | 3.96 (4) |
| Phe | 1.01 (1) | 0.99 (1) | 0.90 (1) | 0.99 (1) | 1.97 (2) |
| Lys | 3.98 (4) | 3.95 (4) | 3.01 (3) | 2.85 (3) | 2.87 (3) |
| His | 2.65 (3) | 2.63 (3) | 2.60 (3) | 2.77 (3) | 2.77 (3) |
| Trp | 0.96 (1) | 0.94 (1) | 0.93 (1) | 0.93 (1) | 0.91 (1) |
| Arg | 2.01 (2) | 2.01 (2) | 1.96 (2) | 1.92 (2) | 1.92 (2) |
| Other Amino Acids | | | | | |
| HPLC retention time (minutes) (C) | 25.3 | 26.4 | 26.3 | 26.5 | 26.3 |

TABLE 2-4

| Amino acid | (18) | (19) | (20) | (21) | (22) |
|---|---|---|---|---|---|
| Asx | 2.00 (2) | 2.00 (2) | 2.00 (2) | 3.00 (3) | 3.00 (3) |
| Ser | 2.66 (3) | 1.78 (2) | 2.65 (3) | 2.34 (3) | 2.55 (3) |
| Glx | 6.75 (6) | 6.67 (6) | 6.65 (6) | 6.04 (6) | 6.00 (6) |
| Gly | 1.05 (1) | 1.05 (1) | 1.06 (1) | 1.04 (1) | 1.02 (1) |
| Val | 2.96 (3) | 2.91 (3) | 2.92 (3) | 2.71 (3) | 2.69 (3) |
| Met | 1.99 (2) | 1.93 (2) | 1.94 (2) | 1.91 (2) | 1.89 (2) |

TABLE 2-4-continued

| Amino acid | (18) | (19) | (20) | (21) | (22) |
|---|---|---|---|---|---|
| Ile | 1.02 (1) | 1.00 (1) | 1.01 (1) | 0.95 (1) | 0.94 (1) |
| Leu | 4.21 (4) | 4.14 (4) | 3.12 (3) | 4.80 (5) | 4.76 (5) |
| Phe | 2.24 (2) | 2.20 (2) | 2.21 (2) | 0.92 (1) | 0.92 (1) |
| Lys | 3.07 (3) | 4.02 (4) | 3.97 (4) | 4.07 (4) | 2.02 (2) |
| His | 2.84 (3) | 2.82 (3) | 2.77 (3) | 1.76 (2) | 2.63 (3) |
| Trp | 0.99 (1) | 1.01 (1) | 0.95 (1) | 0.94 (1) | 0.85 (1) |
| Arg | 2.00 (2) | 1.97 (2) | 1.98 (2) | 2.00 (2) | 1.97 (2) |
| Other Amino Acids | Aib (1) | Aib (1) | Aib (1) | | Orn 1.00 (1) |
| HPLC retention time (minutes) (C) | 26.9 | 26.2 | 24.2 | 26.1 | 25.9 |

TABLE 2-5

| Amino acid | (23) | (24) | (25) |
|---|---|---|---|
| Asx | 4.00 (4) | 4.00 (4) | 3.00 (3) |
| Ser | 2.20 (3) | 2.43 (3) | 2.32 (3) |
| Glx | 3.93 (4) | 4.99 (5) | 6.05 (6) |
| Gly | 0.98 (1) | 0.99 (1) | 0.98 (1) |
| Val | 2.67 (3) | 1.81 (2) | 2.72 (3) |
| Met | 1.92 (2) | 1.95 (2) | 2.22 (2) |
| Ile | 0.92 (1) | 0.95 (1) | 0.93 (1) |
| Leu | 4.80 (5) | 4.90 (5) | 4.95 (5) |
| Phe | 0.95 (1) | 0.96 (1) | 1.00 (1) |
| Lys | 2.98 (3) | 3.04 (3) | 1.92 (2) |
| His | 2.77 (3) | 2.83 (3) | 2.77 (3) |
| Trp | 0.88 (1) | 0.94 (1) | 0.89 (1) |

TABLE 2-5-continued

| Amino acid | (23) | (24) | (25) |
|---|---|---|---|
| Arg | 2.90 (3) | 2.96 (3) | 2.80 (3) |
| Other Amino Acids | | | |
| HPLC retention time (minutes) (C) | 25.2 | 24.1 | 26.0 |

TABLE 3

| Compound | cAMP increase (pmol/well) |
|---|---|
| (6) [Asp$^{10}$, Ala(2-Naph)$^{11}$]hPTH(1-34) | 2.65 |
| (3) [Asp$^{10}$]hPTH(1-34) | 0.60 |
| (4) [Glu$^{10}$]hPTH(1-34) | 1.81 |
| (5) [Asp$^{10}$, Phe$^{11}$]hPTH(1-34) | 2.58 |

EXAMPLE 2

Assay of Biological Activity in vitro of PTH(1–34) Peptide Derivatives

The biological activity of the PTH(1–34) peptide analogues was evaluated by the method reported by Shigeno et al., *The Journal of Biological Chemistry*, 263, 18369–18377 (1988) with a modification. A culture solution (Hank's solution, containing 20 mM N-2-hydroxyethylpiperazine-N'-2-ethanesulfonic acid (HEPES), 0.1% bovine serum albumin and 0.5 mM isobutylmethyl-xanthine) containing a 0.01, 0.1, 1, 10 or 100 nM peptide derivative was added in an amount of 100 μl to a mouse cranial bone-derived osteoblast-like cell strain, MC3T3-EI cells, cultivated on a 96-well multiplate (Nunclon, Nunc), followed by reaction at room temperature for 30 minutes. After addition of 100 μl of 0.2N hydrochloric acid, the plate was immersed in boiling water for 2.5 minutes to extract cyclic adenosine monophosphate (cAMP) produced by a PTH receptor from the cells. The total cAMP in the culture solution and the cells was assayed using a commercial radioimmunoassay kit (cyclic AMP [$^{125}$I] kit "Du Pont-Daiichi", Daiichi Kagaku Yakuhin). For the biological activity of the PTH(1–34) peptide derivatives, increases in cAMP caused by 1 nM analogues are shown in Table 3.

EXAMPLE 3

Assay of Biological Activity of PTH(1–34) Peptide Derivatives

To four-week-old male Sprangue Dawley rats, the compounds synthesized in Example 1 were each subcutaneously given in a dose of 4.9 nmol/kg a day for two weeks, and increases in the bone weight in their femurs were compared with that of a group to which a vehicle (0.15M NaCl, 0.001N hydrochloric acid and 2% heat-inactivated rat serum) was given. After administration, their right femurs were taken out, and the tissues around them were removed. Then, the femurs were dried at 100° C. for 3 hours and weighed. Increases in the bone weight in the rats given the compounds in a dose of 4.9 nmol/kg a day are shown in Table 4.

TABLE 4

| Compound | bone increase (mg) |
|---|---|
| (3) [Asp$^{10}$]hPTH(1-34) | 26.1 |
| (4) [Glu$^{10}$]hPTH(1-34) | 31.1 |
| (5) [Asp$^{10}$, Phe$^{11}$]hPTH(1-34) | 20.4 |
| (19) [Asp$^{10}$, Phe$^{11}$, Lys$^{16,17}$, Gln$^{27}$, Aib$^{30}$]hPTH(1-34) | 16.9 |
| (10) [Glu$^{10}$, Phe$^{11}$, D-Ala$^{12}$]hPTH(1-34) | 19.4 |
| (22) [Glu$^{10}$, Orn$^{13}$]hPTH(1-34) | 14.8 |
| (15) [Glu$^{10}$, Ser$^{16}$]hPTH(1-34) | 15.1 |
| (17) [Glu$^{10}$, Phe$^{11}$, Lys$^{16}$, Gln$^{27}$]hPTH(1-34) | 12.4 |
| (1) [Asp$^{10}$, Lys$^{11}$]hPTH(1-34) | 66.6* |

*: Increase when continuously administered for 4 weeks

What is claimed is:

1. A peptide having the following amino acid sequence or a salt thereof:

Ser-Val-Ser-Glu-lle-Gln-Leu-Met-His-$R_1$-$R_2$-$R_3$-$R_4$-$R_5$-$R_6$-$R_7$-Met-$R_8$-Arg-$R_9$-Glu-Trp-Leu-Arg-$R_{10}$-$R_{11}$-Leu-Gln-$R_{12}$-Val-His-Asn-$R_{13}$ (SEQ ID NO:2), wherein $R_1$ represents Asp or Glu; $R_2$ represents Phe, Lys, Leu or Ala (2-Naph); $R_3$ represents Gly, D-Ala; $R_4$ represents Orn or Lys; $R_5$ represents His; $R_6$ represents Leu; $R_7$ represents Asn-Ser; Lys-Lys, Lys-Ser or Ser-Ser; $R_8$ represents Glu; $R_9$ represents Val; $R_{10}$ represents Lys; $R_{11}$ represents Lys or Gln; $R_{12}$ represents Asp or 2-aminoisobutyric acid and $R_{13}$ represents Phe.

2. The peptide or the salt thereof as claimed in claim 1, wherein said peptide or salt thereof is [$Asp^{10}$] hPTH (1–34).

3. The peptide or the salt thereof as claimed in claim 1, wherein said peptide or salt thereof is [$Glu^{10}$]hPTH(1–34).

4. The peptide or the salt thereof as claimed in claim 1, wherein said peptide or salt thereof is [$Asp^{10}$,$Phe^{11}$]hPTH (1–34).

5. (new) The peptide or the salt thereof as claimed in claim 1, wherein said peptide or salt thereof is [$Asp^{10}$,$Phe^{11}$,$Lys^{16,17}$,$Gln^{27}$,$Aib^{30}$]hPTH(1–34).

6. The peptide or the salt thereof as claimed in claim 1, wherein said peptide or salt thereof is [$Glu^{10}$,$Phe^{11}$,$D-Ala^{12}$] hPTH(1–34).

7. The peptide or the salt thereof as claimed in claim 1, wherein said peptide or salt thereof is [$Glu^{10}$,$Orn^{13}$]hPTH (1–34).

8. The peptide or the salt thereof as claimed in claim 1, wherein said peptide or salt thereof is [$Glu^{10}$,$Ser^{16}$]hPTH (1–34).

9. The peptide or the salt thereof as claimed in claim 1, wherein said peptide or salt thereof is [$Glu^{10}$,$Phe^{11}$,$Lys^{16}$, $Gln^{27}$]hPTH(1–34).

10. The peptide or the salt thereof as claimed in claim 1, wherein said peptide or salt thereof is [$Asp^{10}$,Ala(2-Naph)$^{11}$]hPTH(1–34).

11. The peptide or the salt thereof as claimed in claim 1, wherein said peptide or salt thereof is [$Asp^{10}$,$Lys^{11}$]hPTH (1–34).

12. The peptide or the salt thereof as claimed in 1, wherein $R_2$ represents Leu, $R_7$ represents Asn-Ser and $R_{11}$ represents Lys.

* * * * *